(12) United States Patent
Geva et al.

(10) Patent No.: US 9,839,392 B2
(45) Date of Patent: Dec. 12, 2017

(54) METHOD AND SYSTEM FOR ESTIMATING BRAIN CONCUSSION

(75) Inventors: Amir B. Geva, Tel-Aviv (IL); Amit Reches, Binyamina (IL); Ronen Gadot, Tzur-Yigal (IL)

(73) Assignee: Elminda Ltd., Herzliya (IL)

( * ) Notice: Subject to any disclaimer, the term of this patent is extended or adjusted under 35 U.S.C. 154(b) by 418 days.

(21) Appl. No.: 14/233,788

(22) PCT Filed: Jul. 19, 2012

(86) PCT No.: PCT/IL2012/050262
§ 371 (c)(1),
(2), (4) Date: Jan. 20, 2014

(87) PCT Pub. No.: WO2013/011515
PCT Pub. Date: Jan. 24, 2013

(65) Prior Publication Data
US 2014/0163328 A1 Jun. 12, 2014

Related U.S. Application Data

(60) Provisional application No. 61/509,651, filed on Jul. 20, 2011.

(51) Int. Cl.
*A61B 5/00* (2006.01)
*A61B 5/048* (2006.01)
(Continued)

(52) U.S. Cl.
CPC ............ *A61B 5/4848* (2013.01); *A61B 5/048* (2013.01); *A61B 5/0484* (2013.01);
(Continued)

(58) Field of Classification Search
CPC ..... A61B 5/4848; A61B 5/048; A61B 5/0484; A61B 5/4064; G06F 19/3431; G06F 19/3443
(Continued)

(56) References Cited

U.S. PATENT DOCUMENTS 6,792,304 B1 9/2004 Silberstein
7,720,530 B2 5/2010 Causevic
(Continued)

FOREIGN PATENT DOCUMENTS

CN 101155548 4/2008
CN 102014742 4/2011
(Continued)

OTHER PUBLICATIONS

Notification of Office Action and Search Report dated Dec. 1, 2014 From the State intellectual Property Office of the People's Republic of China Re. Application No. 201180014613.5.
(Continued)

*Primary Examiner* — Carl H Layno
*Assistant Examiner* — Erin M Piateski

(57) ABSTRACT

A method of estimating the likelihood of brain concussion from neurophysiological data acquired from the brain of the subject is disclosed. The method comprises: identifying activity-related features in the data; constructing a subject-specific brain network activity (BNA) pattern having a plurality of nodes, wherein each node represents a feature of the activity-related features, and each pair of nodes is assigned with a connectivity weight; calculating a BNA pattern similarity describing a comparison between the constructed BNA pattern and a baseline BNA pattern being specific to the subject; and assessing the likelihood of brain concussion responsively to the BNA pattern similarity.

32 Claims, 11 Drawing Sheets

(51) Int. Cl.
*A61B 5/0484* (2006.01)
*G06F 19/00* (2011.01)
(52) U.S. Cl.
CPC ........ *A61B 5/4064* (2013.01); *G06F 19/3431* (2013.01); *G06F 19/3443* (2013.01)
(58) Field of Classification Search
USPC .......................................................... 600/300
See application file for complete search history.

(56) References Cited

U.S. PATENT DOCUMENTS

| | | | |
|---|---|---|---|
| 8,320,649 | B2 | 11/2012 | Shahaf et al. |
| 2004/0059241 | A1 | 3/2004 | Suffin |
| 2004/0152995 | A1 | 8/2004 | Cox et al. |
| 2005/0165327 | A1* | 7/2005 | Thibault ............... A61B 3/0066 600/558 |
| 2005/0177058 | A1 | 8/2005 | Sobell |
| 2006/0004422 | A1* | 1/2006 | De Ridder ........... A61N 1/0529 607/45 |
| 2008/0103547 | A1* | 5/2008 | Okun .................. A61N 1/36082 607/45 |
| 2008/0208073 | A1* | 8/2008 | Causevic ............... A61B 5/048 600/544 |
| 2009/0297000 | A1 | 12/2009 | Shahaf et al. |
| 2010/0022907 | A1 | 1/2010 | Perez-Velazquez |
| 2010/0191139 | A1 | 7/2010 | Jacquin et al. |
| 2011/0060266 | A1* | 3/2011 | Streeter ................ A61N 5/0613 604/20 |
| 2012/0296569 | A1 | 11/2012 | Shahaf et al. |

FOREIGN PATENT DOCUMENTS

| | | | |
|---|---|---|---|
| CN | 102906752 | | 1/2013 |
| JP | 07-040445 | | 2/1995 |
| JP | 2002-507940 | | 3/2002 |
| JP | 2004-530475 | | 10/2004 |
| JP | 2008-098280 | | 4/2008 |
| JP | 2009-528103 | | 8/2009 |
| JP | 2009-542351 | | 12/2009 |
| WO | WO 98/56566 | | 12/1998 |
| WO | WO 00/47278 | | 8/2000 |
| WO | WO 02/091119 | | 11/2002 |
| WO | WO 2005/079332 | | 9/2005 |
| WO | WO 2006/094797 | | 9/2006 |
| WO | WO 2007/098957 | | 9/2007 |
| WO | WO 2007/138579 | | 12/2007 |
| WO | WO 2007138579 | A2 * | 12/2007 ......... G06K 9/00543 |
| WO | WO 2008/005513 | | 1/2008 |
| WO | WO 2009/069134 | | 6/2009 |
| WO | WO 2009/069135 | | 6/2009 |
| WO | WO 2009/069136 | | 6/2009 |
| WO | WO 2009/129279 | | 10/2009 |
| WO | WO 2011/086563 | | 7/2011 |
| WO | WO 2013/011515 | | 1/2013 |

OTHER PUBLICATIONS

International Preliminary Report on Patentability dated Jan. 30, 2014 From the International Bureau of WIPO Re. Application No. PCT/IL2012/050262.
Lirdprapamongkol et al. "A Flavonoid Chrysin Suppresses Hypoxic Survival and Metastatic Growth of Mouse Breast Cancer Cells", Oncology Reports, 30: 2357-2364, 2013.
Patent Examination Report dated Apr. 20, 2016 From the Australian Government, IP Australia Re. Application No. 2012285379.
Pre-Examination Processing Notice dated Feb. 16, 2016 From the Australian Government, IP Australia Re. Application No. 2012285379.
Notice of Reasons for Rejection dated Dec. 15, 2015 From the Japanese Patent Office Re. Application No. 2012-548537 and Its Translation Into English.
Communication Pursuant to Article 94(3) EPC dated May 4, 2015 From the European Patent Office Re. Application No. 12750826.5.
Office Action dated Apr. 29, 2015 From the Israel Patent Office Re. Application No. 221019.
Notification of Office Action dated Sep. 29, 2015 From the State Intellectual Property Office of the People's Republic of China Re. Application No. 201180014613.5 and Its Translation Into English.
Official Action dated Dec. 17, 2014 From the US Patent and Trademark Office Re. U.S. Appl. No. 13/522,747.
Translation Dated Dec. 16, 2014 of Notification of Office Action and Search Report dated Dec. 1, 2014 From the State Intellectual Property Office of the People's Republic of China Re. Application No. 201180014613.5.
Stam et al. "Graph Theoretical Analysis of Complex Networks in the Brain", Nonlinear Biomedial Physics, 1(3): 1-19, Jul. 5, 2007.
Notification of Office Action and Search Report dated Mar. 3, 2016 From the State Intellectual Property Office of the People's Republic of China Re. Application No. 201280045473.2 and Its Translation Into English.
Communication Pursuant to Article 94(3) EPC dated Mar. 9, 2016 From the 12750826.5. European Patent Office Re. Application No. 12750826.5.
Official Action dated Dec. 4, 2015 From the US Patent and Trademark Office Re. U.S. Appl. No. 13/522,747.
Notification of Office Action and Search Report dated Nov. 10, 2015 From the State Intellectual Property Office of the People's Republic of China Re. Application No. 201280045473.2.
Translation Dated Nov. 24, 2015 of Notification of Office Action and Search Report dated Nov. 10, 2015 From the State Intellectual Property Office of the People's Republic of China Re. Application No. 201280045473.2.
Notice of Reasons for Refusal dated Jun. 19, 2015 From the Japanese Patent Office Re. Application No. 2012-548537 and Its Translation Into English.
Notification of Office Action and Search Report dated Apr. 9, 2015 From the State Intellectual Property Office of the People's Republic of China Re. Application No. 201280045473.2 and Its Translation Into English.
International Preliminary Report on Patentability dated Aug. 2, 2012 From the International Bureau of WIPO Re. Application No. PCT/IL2011/000055.
International Search Report and the Written Opinion dated Feb. 7, 2012 From the International Searching Authority Re. Application No. PCT/IL2011/000055.
International Search Report and the Written Opinion dated Nov. 7, 2012 From the International Searching Authority Re. Application No. PCT/IL2012/050262.
Restriction Official Action dated Aug. 27, 2013 From the US Patent and Trademark Office Re. U.S. Appl. No. 13/522,747.
Doyle et al. "Attention-Deficit/Hyperactivity Disorder Endophenotypes", Biological Psychiatry, XP004932899, 57(11): 1324-1335, Jun. 1, 2005. Section 'Electrophysiology: Association With ADHD', p. 1330.
Reijneveld et al. "The Application of Graph Theoretical Analysis to Complex Networks in the Brain", Clinical Neurophysiology, XP022295008, 118(11): 2317-2331, Oct. 11, 2007.
Official Action dated Feb. 18, 2014 From the US Patent and Trademark Office Re. U.S. Appl. No. 13/522,747.
Notice of Reasons for Refusal dated Sep. 24, 2014 From the Japanese Patent Office Re. Application No. 2012-548537 and Its Translation Into English.
Translation Dated May 18, 2015 of Office Action dated Apr. 29, 2015 From the Israel Patent Office Re. Application No. 221019.
Notice of Reason for Rejection dated Apr. 26, 2016 From the Japanese Patent Office Re. Application No. 2014-520791 and Its Translation Into English.
Notification of Office Action and Search Report dated May 5, 2016 From the State Intellectual Property Office of the People's Republic of China Re. Application No. 201180014613.5 and Its Translation Into English.
Request for Examination dated May 4, 2016 From the Rospatent, Federal Government Institution, Federal Institute of Industrial Property of the Federal Service of Intellectual Property, Patent and

(56) References Cited

OTHER PUBLICATIONS

Trademarks of the Russian Federation Re. Application No. 2014105665 and Its Translation Into English.
Official Action dated Sep. 8, 2016 From the US Patent and Trademark Office Re. U.S. Appl. No. 13/522,747.
Notification of Office Action and Search Report dated Nov. 7, 2016 From the State Intellectual Property Office of the People's Republic of China Re. Application No. 201180014613.5. (5 Pages).
Translation of Notification of Office Action and Search Report dated Nov. 7, 2016 From the State Intellectual Property Office of the People's Republic of China Re. Application No. 201180014613.5. (5 Pages).
Communication Pursuant to Article 94(3) EPC dated Mar. 31, 2017 From the European Patent Office Re. Application No. 11705277.9. (11 Pages).
Notice of Reasons for Refusal dated May 22, 2015 From the Japan Patent Office Re. Application No. 2016-114846 and Its Translation Into English. (7 Pages).
Office Action dated Apr. 5, 2017 From the Israel Patent Office Re. Application No. 230502 and Its Translation Into English. (7 Pages).
Notice of Reason for Rejection dated Dec. 16, 2016 From the Japanese Patent Office Re. Application No. 2014-520791 and Its Translation Into English. (5 Pages).
Office Action dated Jan. 23, 2017 From the Israel Patent Office Re. Application No. 221019 and Its Translation Into English. (6 Pages).
Requisition by the Examiner dated Jan. 9, 2017 From the Canadian Intellectual Property Office Re. Application No. 2,786,380. (12 Pages).
Request for Examination Dated Aug. 24, 2017 From the ROSPATENT, Federal Government Institution, Federal Institute of Industrial Property of the Federal Service of Intellectual Property, Patent and Trademarks of the Russian Federation Re. Application No. 2014105665 and Its Translation Into English. (15 pages).

\* cited by examiner

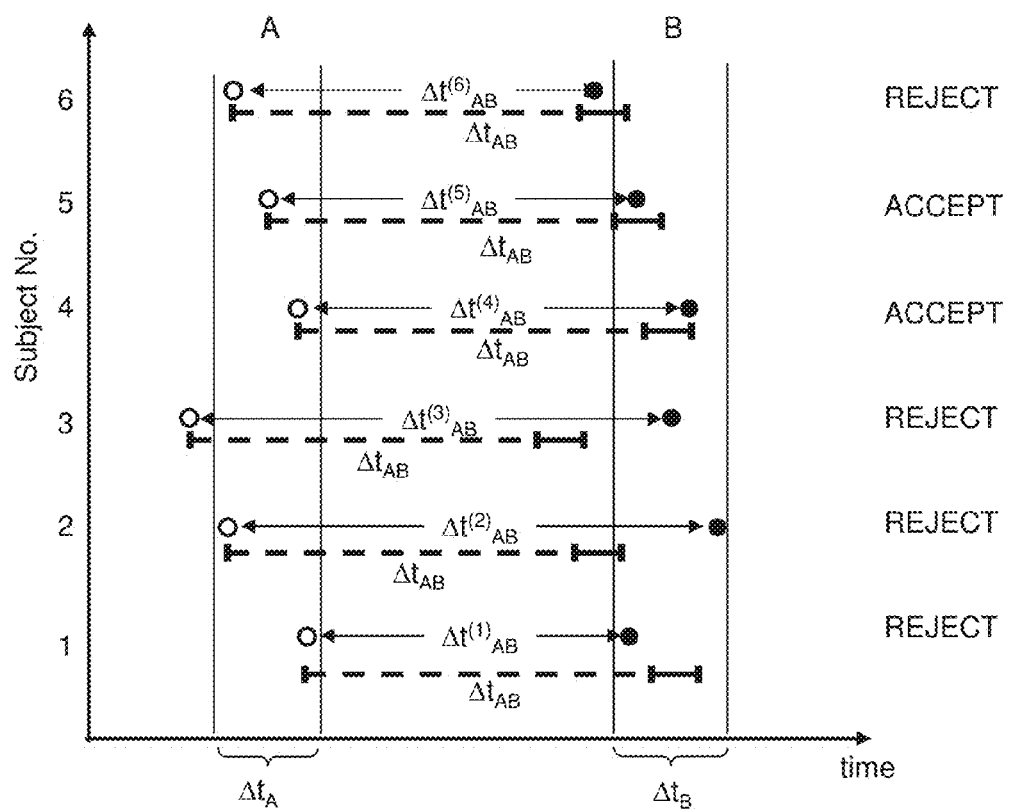
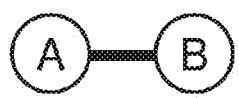 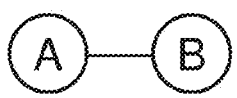 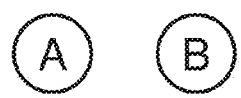
FIG. 2B
FIG. 2C  FIG. 2D  FIG. 2E

METHOD AND SYSTEM FOR ESTIMATING BRAIN CONCUSSION

RELATED APPLICATIONS

This application is a National Phase of PCT Patent Application No. PCT/IL 2012/050262 having International filing date of Jul. 19, 2012, which claims the benefit of priority under 35 USC §119(e) of U.S. Provisional Patent Application No. 61/509,651 filed Jul. 20, 2011. The contents of the above applications are incorporated herein by reference in their entirety.

The contents of PCT Patent Application No. PCT/IL2011/000055 filed on Jan. 18, 2011 are hereby incorporated by reference as if fully set forth herein.

FIELD AND BACKGROUND OF THE INVENTION

The present invention, in some embodiments thereof, relates to neurophysiology and, more particularly, but not exclusively, to method and system for estimating the likelihood of brain concussion.

Mild traumatic brain injury (mTBI), commonly known as brain concussion, or simply "concussion," describes an insult to the head that, in turn, causes an injury to the brain. It most often occurs from direct contact to the head but can also result from indirect injury (e.g., whiplash injury or violent shaking of the head).

The brain is a soft, jell-like structure covered with a dense network of blood vessels and contains billions of nerve cells and a complexity of interconnecting fibers. The brain is a well-protected part of the body enclosed in the skull and cushioned in the cerebrospinal fluid. A head trauma, such as a direct impact to the head or rapid movement thereof, can cause the brain to rebound against the skull, potentially causing a tearing and twisting of the structures and blood vessels of the brain resulting in a disturbance of function of the electrical activity of the nerve cells in the brain and a breakdown of the usual flow of messages within the brain. A head trauma can cause multiple shearing injuries which stretch and tear the soft nerve tissue and cause multiple points of bleeding from small blood vessels of the brain.

Individuals who have suffered one brain injury are more at risk for a second brain injury and more susceptible for subsequent injuries. Regardless of the severity, the second injury to the brain can be life-threatening if incurred within a short time interval. Additional risks from a series of concussions include premature senility and Alzheimer's disease.

There is a concern in various contact sports, such as football, hockey and soccer, of brain concussion due to impact to the head. During such physical activity, the head or other body part of the individual is often subjected to direct contact to the head which results in impact to the skull and brain of the individual as well as movement of the head or body part itself. Much remains unknown about the response of the brain to head accelerations in the linear and rotational directions and even less about the correspondence between specific impact forces and injury, particularly with respect to injuries caused by repeated exposure to impact forces of a lower level than those that result in a catastrophic injury or fatality.

Neurophysiological activity is altered following traumatic brain injury resulting, in the initial phases of post-injury, in neuronal hyperexcitability. Electrophysiological analysis of patients with cerebral trauma and concussion was first reported in the 1970's. It was proposed that the analysis of the coherence of post traumatic EEG waves may detect and quantify diffuse axonal injury.

Known in the art are methods for identifying brain injury.

U.S. Pat. No. 7,720,530 discloses a method for providing an on-site diagnosis of a subject to determine the presence and severity of a concussion. EEG signals are acquired from the subject. The signals are processed using a non-linear signal processing algorithm which denoises the detected signals, extracts features from the denoised signals, builds discriminant functions for classifying the extracted features, and detects the presence and severity of a concussion based on the classified features.

U.S. Published Application No. 20100022907 teaches that phase synchronization in an EEG signal is indicative of a site of brain injury.

Also known are general techniques that identify discrete participating regions for the purpose of relating behavioral functions to their underlying localized brain activities, or perform flow analysis.

U.S. Pat. No. 6,792,304 discloses a method and a system for mass communication assessment. A cognitive task is transmitted from a central control site to a plurality of remote test sites via Internet. The brain response of the subjects at the remote sites in response to the task is recorded and transmitted back to the central control site via the Internet. The central control site then computes the variations in the brain activities for the subjects at each of the selected sites.

U.S. Published Application No. 20040059241 discloses a method for classifying and treating physiologic brain imbalances. Neurophysiologic techniques are used for obtaining a set of analytic brain signals from a subject, and a set of digital parameters is determined from the signals. The digital parameters are quantitatively mapped to various therapy responsivity profiles. The signals and parameters for a subject are compared to aggregate neurophysiologic information contained in databases relating to asymptomatic and symptomatic reference populations, and the comparison is used for making treatment recommendations. Treatment response patterns are correlated as a dependent variable to provide a connection to successful outcomes for clinical treatment to of afflicted subjects.

International Publication No. WO 2007/138579, the contents of which are hereby incorporated by reference, describes a method for establishing a knowledge base of neuropsychological flow patterns. Signals from multiple research groups for a particular behavioral process are obtained, and sources of activity participating in the particular behavioral functions are localized. Thereafter, sets of patterns of brain activity are identified, and neuropsychological analysis is employed for analyzing the localized sources and the identified patterns. The analysis includes identification and ranking of possible pathways. A set of flow patterns is then created and used as a knowledge base. The knowledge base is then used as a constraint for reducing the number of ranked pathways.

International Publication Nos. WO 2009/069134, WO 2009/069135 and WO 2009/069136, the contents of which are hereby incorporated by reference, describe a technique in which neurophysiological data are collected before and after the subject has performed a task and/or action that forms a stimulus. The stimulus is used for defining features in the data, and the data are decomposed according to the defined features. Thereafter, the features are analyzed to determine one or more patterns in the data. The decomposition can employ clustering for locating one or more important features in the data, wherein a collection of clusters forms an activity network. The data patterns can be analyzed for defining a neural model which can be used for simulating the effect of a particular pathology and/or treatment on the brain.

Additional background art includes U.S. Published Application No. 20050177058, which discloses a system in which EEG readings from more than one subject at the same or different locations are collected, analyzed and compared, when they are exposed to a common set of stimuli. The compatibility of the subjects is studied using their EEG readings, and concealed information is discovered or verified from.

SUMMARY OF THE INVENTION

According to an aspect of some embodiments of the present invention there is provided a method of estimating the likelihood of brain concussion from neurophysiological data acquired from the brain of the subject. The method comprises: identifying activity-related features in the data; constructing a subject-specific brain to network activity (BNA) pattern having a plurality of nodes, wherein each node represents a feature of the activity-related features, and each pair of nodes is assigned with a connectivity weight; calculating a BNA pattern similarity describing a comparison between the constructed BNA pattern and a baseline BNA pattern being specific to the subject; and assessing the likelihood of brain concussion responsively to the BNA pattern similarity.

According to some embodiments of the invention the baseline BNA pattern is based on a group BNA pattern characterizing a group of subjects indentified as having normal brain function.

According to some embodiments of the invention the baseline BNA pattern is based on a group BNA pattern characterizing a group of subjects indentified as having a brain concussion.

According to some embodiments of the invention the method comprises repeating the construction of subject-specific BNA and the calculation of BNA pattern similarity at least once.

According to some embodiments of the invention each subject-specific BNA is constructed based on different reference data or model but using the same neurophysiological data of the subject, wherein each subject-specific BNA is compared to a baseline BNA pattern being associated with a different brain condition, and wherein the assessment is responsively to at least two BNA pattern similarities.

According to some embodiments of the invention at least one baseline BNA pattern characterizes a group of subjects indentified as having normal brain function, and at least one baseline BNA pattern characterizes a group of subjects indentified as having a brain concussion.

According to some embodiments of the invention the method comprises determining a concussion index based on at least the BNA pattern similarity.

According to some embodiments of the invention the method comprises constructing several BNA patterns corresponding to different time intervals, and displaying the BNA patterns on a time axis.

According to some embodiments of the invention the method comprises extracting prognostic information regarding a brain condition, responsively to at least the BNA pattern similarity.

According to some embodiments of the invention the method comprises identifying features and relations among features in the neurophysiological data of the subject, and comparing the features and the relations among features to features and relations among features of reference neurophysiological data, thereby identifying the activity-related features.

According to some embodiments of the invention the reference neurophysiological data corresponds to data acquired from a group or a sub-group of subjects.

According to some embodiments of the invention the reference neurophysiological data corresponds to history data previously acquired from the same subject.

According to some embodiments of the invention the reference neurophysiological data comprise data synthesized from a neurophysiological model.

According to some embodiments of the invention the features and relations among features of the reference data are provided as at least one previously annotated BNA pattern.

According to some embodiments of the invention the nodes represent clusters of vectors of data characteristics, and wherein the connectivity weight comprises a weight index calculated based on at least one cluster property selected from the group consisting of: (i) a number of vectors in a corresponding pair of clusters; (ii) a variability among numbers of vectors in the corresponding pair of clusters; (iii) a width of time windows associated with each cluster of the corresponding pair of clusters; (iv) a latency difference separating the corresponding pair of clusters; (v) amplitude of a signal associated with the corresponding pair of clusters; (vi) frequency of a signal associated with the corresponding pair of clusters; and (vii) the width of a spatial window defining the clusters.

According to some embodiments of the invention the neurophysiological data comprises data acquired before, during and/or after a treatment.

According to some embodiments of the invention the method comprises assessing the effect of the treatment by comparing a BNA pattern similarity calculated using at least the baseline BNA pattern and a subject-specific BNA pattern constructed based on data acquired before a treatment, to a BNA pattern similarity calculated using at least the baseline BNA pattern and a subject-specific BNA pattern constructed based on data acquired after a treatment.

According to some embodiments of the invention the method comprises assessing the effect of the treatment by comparing a BNA pattern corresponding to data acquired before a treatment to a BNA pattern corresponding to data acquired during and/or after a treatment.

According to some embodiments of the invention the treatment comprises a pharmacological treatment employing an active agent.

According to some embodiments of the invention the active agent is selected from the group consisting of scopolamine, ketamine, methylphenidate, donepezil, physostigmine, tacrine, fluoxetine, carbamazepine, amantadine, apomorphine, bromocriptine, levodopa, pergolide, ropinirole, selegiline, trihexyphenidyl, atropine, scopolamine, glycopyrrolate, baclofen, diazepam, tizanidine and dantrolene.

According to some embodiments of the invention the method according to any wherein the treatment also comprises a placebo treatment employing a placebo agent, and wherein the method comprises assessing the effect of the pharmacological treatment by comparing a BNA pattern corresponding to data acquired during and/or after the a placebo treatment to a BNA pattern corresponding to data acquired during and/or after the pharmacological treatment.

According to some embodiments of the invention the treatment comprises a surgical intervention.

According to some embodiments of the invention the treatment comprises a rehabilitative treatment.

According to some embodiments of the invention the treatment comprises phototherapy.

According to some embodiments of the invention the treatment comprises hyperbaric therapy.

According to some embodiments of the invention the treatment comprises at least one treatment selected from the group consisting of neural feedback, EMG biofeedback, EEG neurofeedback, transcranial magnetic stimulation (TMS) and direct electrode stimulation.

According to an aspect of some embodiments of the present invention there is provided a method of estimating the likelihood of brain concussion from neurophysiological data acquired from the brain of the subject. The method comprises: identifying activity-related features in the data; constructing a first subject-specific brain network activity (BNA) pattern having a plurality of nodes, wherein each node represents a feature of the activity-related features, and each pair of nodes is assigned with a connectivity weight, the subject-specific BNA pattern being associated with brain concussion; calculating a first BNA pattern similarity describing a comparison between the first BNA pattern and a first baseline BNA pattern annotated as corresponding to brain concussion; comparing the similarity with a first recorded similarity describing comparison between a previously constructed subject-specific BNA pattern of the subject and the first baseline BNA pattern; and assessing the likelihood of brain concussion responsively to a difference between the recorded similarity and the calculated similarity.

According to some embodiments of the invention the method comprises constructing a second subject-specific BNA pattern associated with normal brain function; calculating a second BNA pattern similarity describing a comparison between the second BNA pattern and a second baseline BNA pattern annotated as corresponding to normal brain function; and comparing the second similarity with a second recorded similarity describing comparison between a previously constructed subject-specific BNA pattern of the subject and the second baseline BNA pattern; wherein the assessment is responsively also to a difference between the second recorded similarity and the second calculated similarity.

According to some embodiments of the invention the method comprises acquiring the neurophysiological data from the brain of the subject, before, during and/or after the subject is performing or conceptualizing performing a task selected from the group consisting of a lower-level cognitive task and a higher-level cognitive task.

According to an aspect of some embodiments of the present invention there is provided a system for estimating the likelihood of brain concussion, comprising, comprising a data processor configured for receiving neurophysiological data, and executing the method as delineated above and optionally as further detailed hereinunder.

According to an aspect of some embodiments of the present invention there is provided a computer software product, comprising a computer-readable medium in which program instructions are stored, which instructions, when read by a data processor, cause the data processor to receive neurophysiological data and execute the method as delineated above and optionally as further detailed hereinunder.

According to an aspect of some embodiments of the present invention there is provided a method of assessing a likelihood of ADHD. The method comprises: identifying activity-related features in neurophysiological data acquired from the brain of a subject; constructing a brain network activity (BNA) pattern having a plurality of nodes, each representing a feature of the activity-related features; and calculating a BNA pattern similarity describing a comparison between the constructed BNA pattern and a baseline BNA pattern, the baseline BNA pattern having nodes representing event related potentials, predominantly at one or more frequency bands selected from the group consisting of delta, theta and alpha frequency bands, at a plurality of frontocentral locations within a characteristic time window of from about 100 ms to about 200 ms, and/or at a delta frequency band at a plurality of occipital, parietal and frontocentral locations within a characteristic time window of from about 300 ms to about 600 ms; wherein a BNA pattern similarity which is above a predetermined threshold indicates a likelihood of the subject having ADHD.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a flowchart diagram of a method suitable for estimating the likelihood of brain concussion, according to various exemplary embodiments of the present invention;

FIG. 2A is a flowchart diagram describing a procedure for identifying activity-related features for a group of subjects, according to some embodiments of the present invention;

FIG. 2B is schematic illustration of a procedure for determining relations between brain activity features, according to some embodiments of the present invention;

Figure 3:
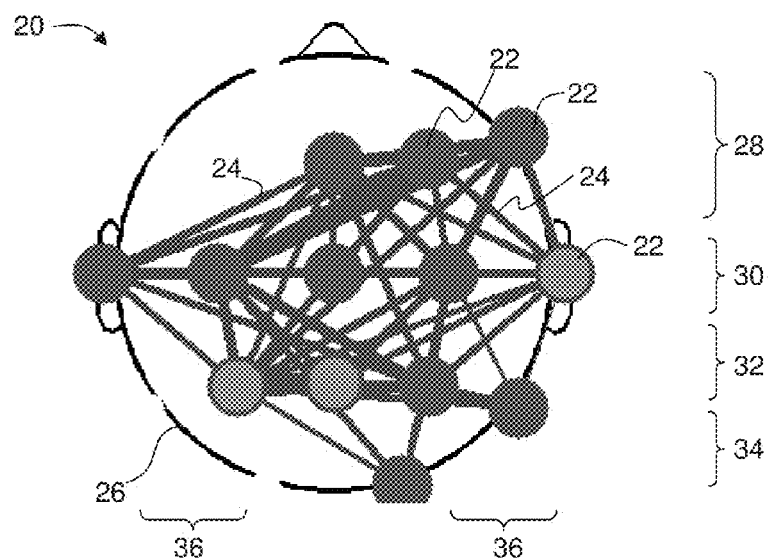
Figure 4:
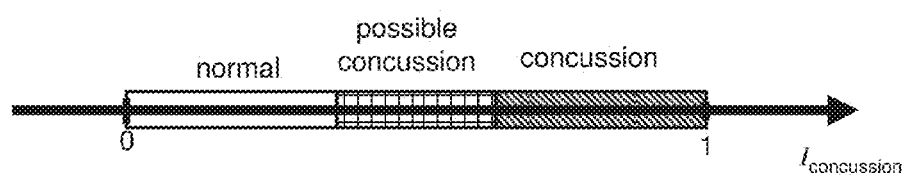
Figure 5:
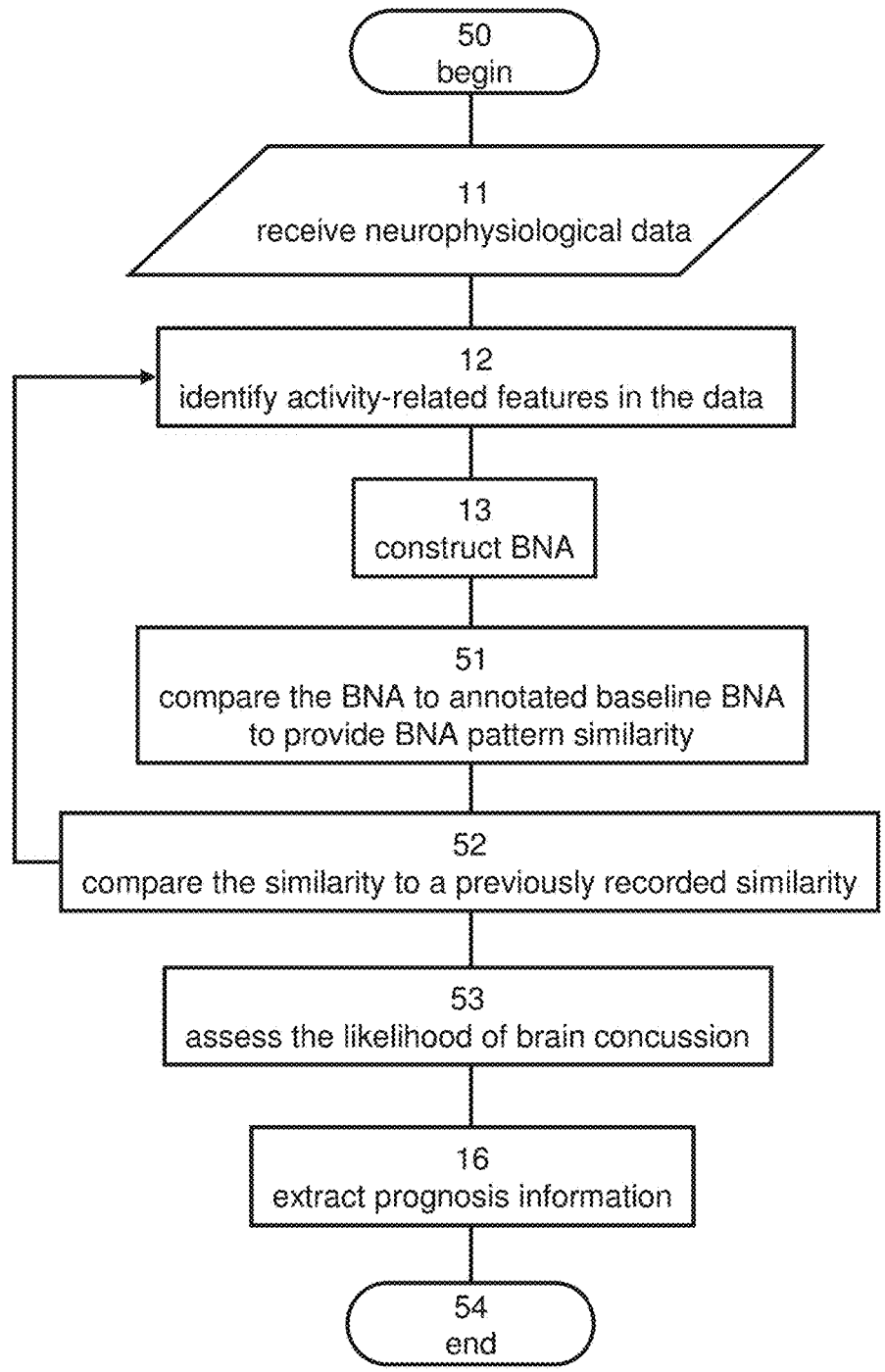
Figure 6A:
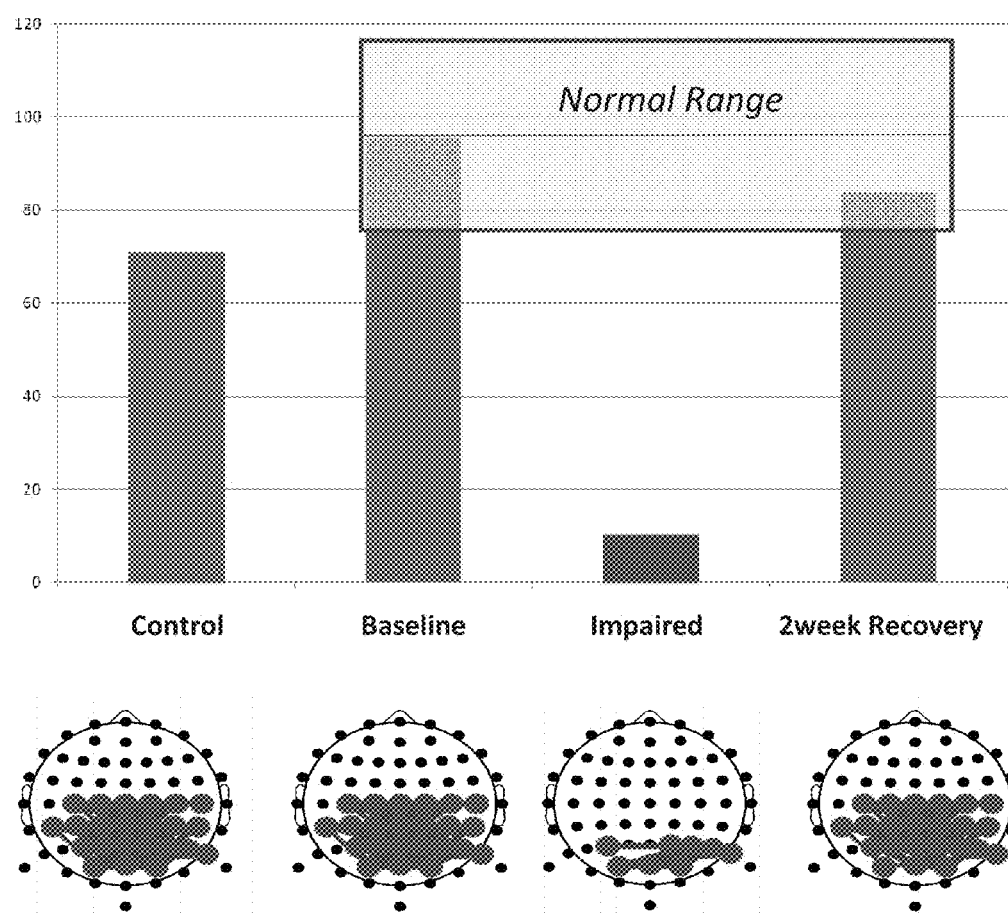
Figure 6B:
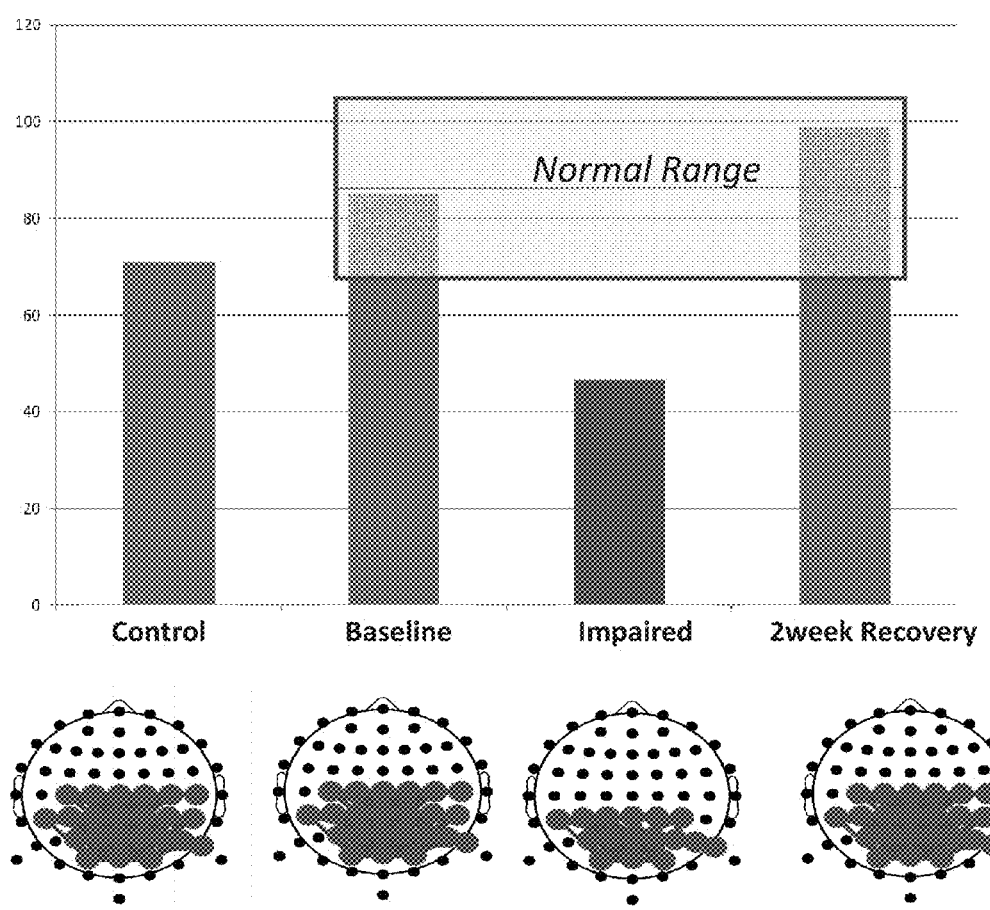
Figure 6C:
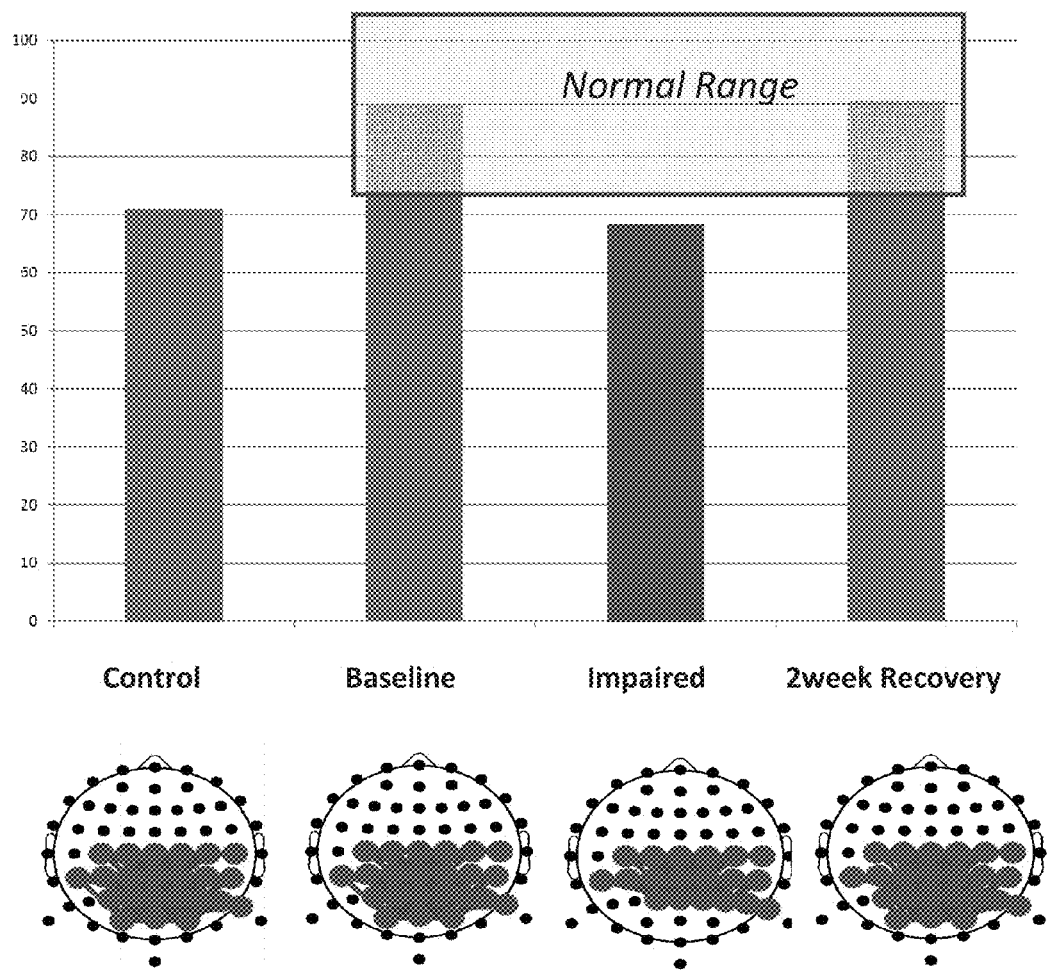
Figure 7A:
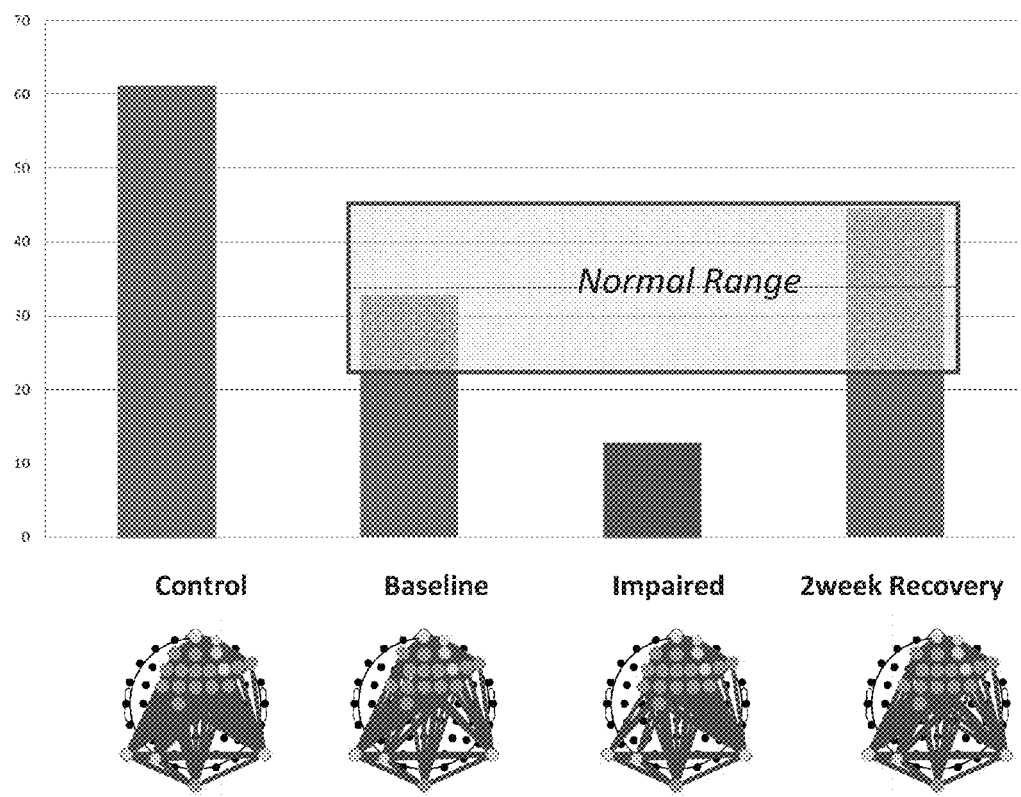
Figure 7B:
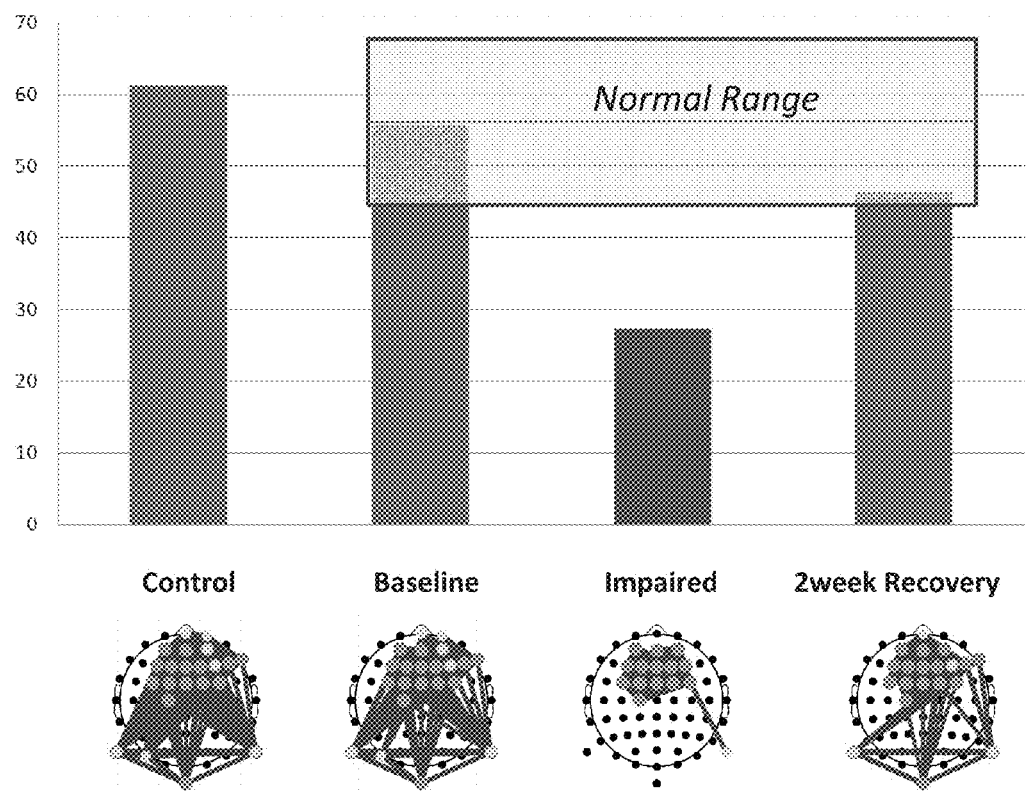
Figure 7C:
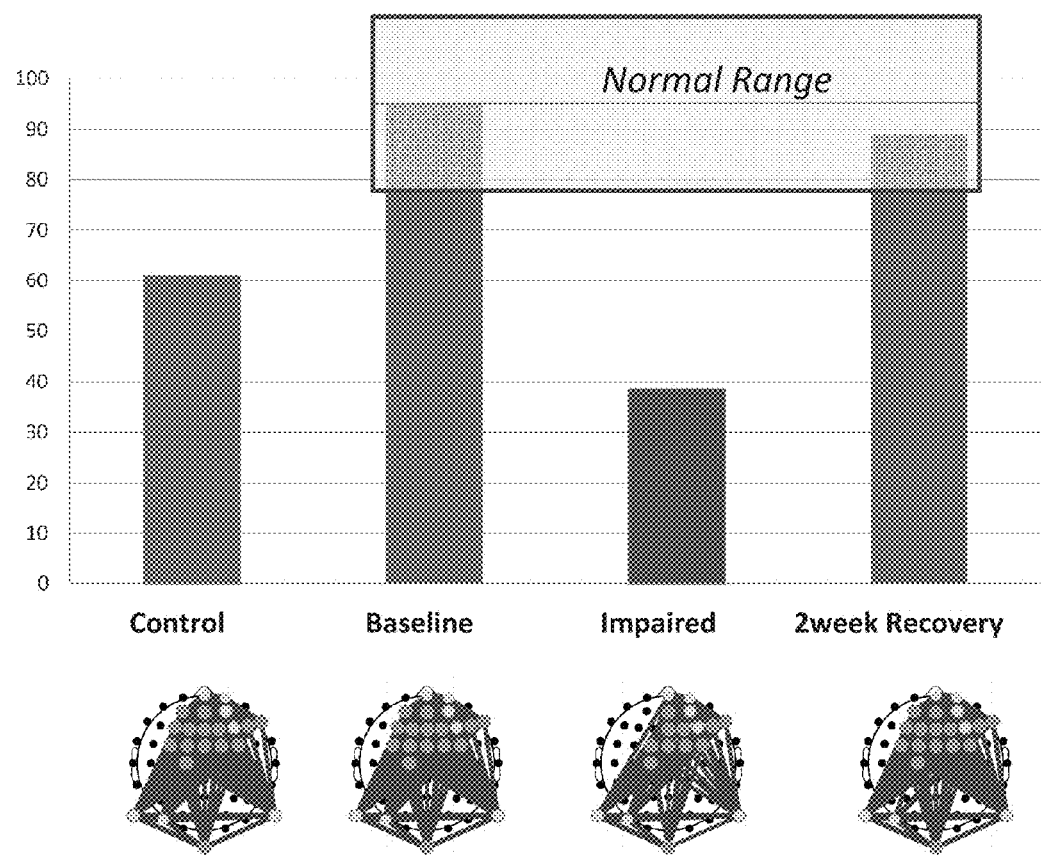

FIGS. 2C-E are abstract illustrations of a BNA patterns constructed according to some embodiments of the present invention using the procedure illustrated in FIG. 2B;

FIG. 3 is a schematic illustration showing a representative example of a Brain Network Activity (BNA) pattern which can be extracted from neurophysiological data, according to some embodiments of the present invention;

FIG. 4 is an illustration of a graphical presentation which can be used in accordance with some embodiments of the present invention to present a brain concussion index;

FIG. 5 is a flowchart diagram of another method suitable for estimating the likelihood of brain concussion, according to some embodiments of the present invention;

FIGS. 6A-C show results of experiments performed for three different subjects suffering from concussion, wherein neurophysiology data were collected during an attention test; and FIGS. 7A-C show results of experiments performed for the same three subjects as in FIGS. 6A-C, respectively, wherein neurophysiology data were collected during working memory test.

DESCRIPTION OF SPECIFIC EMBODIMENTS OF THE INVENTION

The present invention, in some embodiments thereof, relates to neurophysiology and, more particularly, but not exclusively, to method and system for estimating the likelihood of brain concussion.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Traumatic brain injuries (TBI) are often classified into mild, moderate and severe TBI based on three parameters: 1) the quality and length of change in consciousness, 2) the length of amnesia (memory loss), and 3) the Glasgow Coma Scale (GCS). Traditionally, a brain injury is classified as concussion (mTBI) is the length of consciousness is less than 20 minutes and amnesia is 24 hours or less, and is the GCS score is above 13.

It is recognized by the present inventors that a practical diagnostic tool for concussion is not yet available, and that even using the above criteria diagnosing concussion is difficult, since the signs and symptoms of concussion are often very subtle and difficult to detect. In addition, many concussion cases are overshadowed by other injuries or by the events surrounding the injury, further confounding accurate diagnoses. The present inventors found that in the common practice concussion is under-diagnosed or misdiagnosed, resulting in potential long-term consequences for patients, including cognitive deficits, psychosocial problems, and secondary complications such as depression.

The lack of diagnostic aids is especially apparent in athletic settings and can lead to repetitive injuries in children and young adults.

The present inventors have devised a technique which is suitable for estimating the likelihood of concussion using neurophysiological data. Concussions are most commonly suffered from sports-related injuries, and therefore the concern for sports-related brain injuries is higher than ever. Yet, concussion also peaks in the aged population. The present embodiments, therefore, concern with the assessment of likelihood of brain concussion for adult or young subjects who are engaged with sport activities, as well as for aged subjects (e.g., above 60 years).

Figure 1:
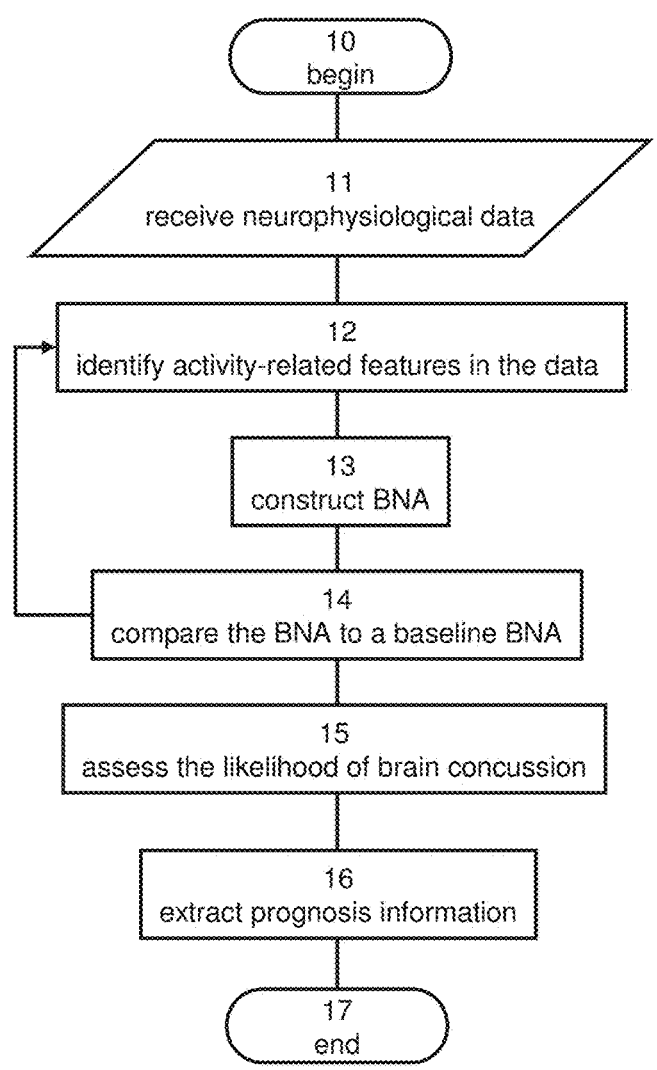

FIG. 1 is a flowchart diagram of a method suitable for of estimating the likelihood of brain concussion from neurophysiological data, according to various exemplary embodiments of the present invention. It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

At least part of the operations can be can be implemented by a data processing system, e.g., a dedicated circuitry or a general purpose computer, configured for receiving the data and executing the operations described below.

Computer programs implementing the method of the present embodiments can commonly be distributed to users on a distribution medium such as, but not limited to, a floppy disk, a CD-ROM, a flash memory device and a portable hard drive. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

The method of the present embodiments can be embodied in many forms. For example, it can be embodied in on a tangible medium such as a computer for performing the method operations. It can be embodied on a computer readable medium, comprising computer readable instructions for carrying out the method operations. In can also be embodied in electronic device having digital computer capabilities arranged to run the computer program on the tangible medium or execute the instruction on a computer readable medium.

The neurophysiological data to be analyzed can be any data acquired directly from the brain of the subject under investigation. The data acquired "directly" in the sense that it shows electrical, magnetic, chemical or structural features of the brain tissue itself. The neurophysiological data can be data acquired directly from the brain of a single subject or data acquired directly from multiple brains of respective multiple subjects (e.g., a research group), not necessarily simultaneously.

Analysis of data from multiple brains can be done by performing the operations described below separately for each portion of the data that correspond to a single brain. Yet, some operations can be performed collectively for more than one brain. Thus, unless explicitly state otherwise, a reference to "subject" or "brain" in the singular form does not necessarily mean analysis of data of an individual subject. A reference to "subject" or "brain" in the singular form encompasses also analysis of a data portion which corresponds to one out of several subjects, which analysis can be applied to other portions as well.

The data can be analyzed immediately after acquisition ("online analysis"), or it can be recorded and stored and thereafter analyzed ("offline analysis").

Representative example of neurophysiological data types suitable for the present invention, include, without limitation, electroencephalogram (EEG) data, magnetoencephalography (MEG) data, computer-aided tomography (CAT) data, positron emission tomography (PET) data, magnetic resonance imaging (MRI) data, functional MRI (fMRI) data, ultrasound data, single photon emission computed tomography (SPECT) data, Brain Computer Interface (BCI) data, and data from neuroprostheses at the neural level. Optionally, the data include combination of two or more different types of data.

In various exemplary embodiments of the invention the neurophysiological data are associated with signals collected using a plurality of measuring devices respectively placed at a plurality of different locations on the scalp of the subject. In these embodiments, the data type is preferably EEG or MEG data. The measuring devices can include electrodes, superconducting quantum interference devices (SQUIDs), and the like. The portion of the data that is acquired at each such location is also referred to as "channel." In some embodiments, the neurophysiological data are associated with signals collected using a plurality of measuring devices placed in the brain tissue itself. In these embodiments, the data type is preferably invasive EEG data, also known as electrocorticography (ECoG) data.

Optionally and preferably, the neurophysiological data is collected at least before and after the subject has performed a task and/or action. In some embodiments of the present invention the neurophysiological data is collected at least before and after the subject has conceptualized a task and/or action but has not actually performed the task. These embodiments are useful when the subject is suffering from some type of physical and/or cognitive deficit that may prevent actual execution of a task and/or action, as for example may be seen in response to various brain injuries such as stroke. Nevertheless, these embodiments can be employed for any subject, if desired.

Neurophysiological data which is associated with a task and/or action (whether actually performed or conceptualized) can be used as event related measures, such as event related potentials (ERPs) or event related fields (ERFs). The task and/or action (whether actually performed or conceptualized) is preferably in response to a stimulus or stimuli, and the acquisition of data is synchronized with the stimulus to establish a timeline of the response and extract data features responsively to this timeline. Typically, but not necessarily, the data collection is on-going such that neurophysiological data are collected continuously before, during and after performance or conceptualization of the task and/or action.

Various types of tasks are contemplated, both lower-level and higher-level cognitive tasks and/or actions. The task/action can be single, serial or on-going. An example of an on-going lower-level cognitive task/action includes, without limitation, watching a movie; an example of a single lower-level cognitive task/action includes, without limitation, providing an audible signal (e.g., a simple sound) to the subject; and an example of a serial lower-level cognitive task/action includes, without limitation, playing an audible signal repeatedly. It is appreciated that for a repetitive task the subject may eventually be conditioned and will pay less attention (a process known as habituation), but there still will be a response from the brain. An example of a higher-level cognitive task/action includes, without limitation, the so called "Go/NoGo task" in which the subject is requested to push a button if a high pitch sound is heard, wherein if a low pitch sound is heard then the subject is not to push the button. This task is known in the art and is used in many cognitive studies.

Many protocols of stimuli and stimuli-responses are known in the art, all of which are contemplated by some embodiments of the present invention. Stimulus-response neuropsychological tests include, without limitation, the Stroop task, the Wisconsin card sorting test, and the like; stimulus-only based tests include, without limitation, mismatch negativity, brain-stem-evoked response audiometry (BERA), and the like. Also contemplated are response-only based tests, such as, but not limited to, saccade analysis, movement related potentials (MRP), N-back memory tasks and other working memory tasks, e.g., the Sternberg memory task, the "serial seven" test (counting back from 100 in jumps of seven), the Posner attention tasks and the like.

It is to be understood that it is not intended to limit the scope of the present invention only to neurophysiological data associated with stimulus, task and/or action. Embodiments of the present invention can be applied also to neurophysiological data describing spontaneous brain activity. Also contemplated are embodiments in which the neurophysiological data are acquired during particular activities, but the acquisition is not synchronized with a stimulus.

Referring now to FIG. 1, the method begins at 10 and optionally and preferably continues to 11 at which the neurophysiological data are received. The data can be recorded directly from the subject or it can be received from an external source, such as a computer readable memory medium on which the data are stored.

The method continues to 12 at which relations between features of the data are determined so as to indentify activity-related features. This can be done using any procedure known in the art. For example, procedures as described in International Publication Nos. WO 2007/138579, WO 2009/069134, WO 2009/069135 and WO 2009/069136, the contents of which are hereby incorporated by reference, can be employed. A detailed description of a procedure suitable for executing 12 according to some embodiments of the present invention is described hereinunder with reference to FIG. 2A.

Broadly speaking, the extraction of activity-related features includes multidimensional analysis of the data, wherein the data is analyzed to extract spatial and non-spatial characteristics of the data.

The spatial characteristics preferably describe the locations from which the respective data were acquired. For example, the spatial characteristics can include the locations of the measuring devices (e.g., electrode, SQUID) on the scalp of the subject.

Also contemplated are embodiments in which the spatial characteristics estimate the locations within the brain tissue at which the neurophysiological data were generated. In these embodiments, a source localization procedure, which may include, for example, low resolution electromagnetic tomography (LORETA), is employed. A source localization procedure suitable for the present embodiments is described in the aforementioned international publications which are incorporated by reference. Other source localization procedure suitable for the present embodiments are found in Greenblatt et al., 2005, "Local Linear Estimators for the Bioelectromagnetic Inverse Problem," IEEE Trans. Signal Processing, 53(9):5430; Sekihara et al., "Adaptive Spatial Filters for Electromagnetic Brain Imaging (Series in Biomedical Engineering)," Springer, 2008; and Sekihara et al., 2005, "Localization bias and spatial resolution of adaptive and non-adaptive spatial filters for MEG source reconstruction," NeuroImage 25:1056; the contents of which are hereby incorporated by reference.

Additionally contemplated are embodiments in which the spatial characteristics estimate locations on the epicortical surface. In these embodiments, data collected at locations on the scalp of the subject are processed so as to map the scalp potential distribution onto the epicortical surface. The technique for such mapping is known in the art and referred to in the literature as Cortical Potential Imaging (CPI) or Cortical Source Density (CSD). Mapping techniques suitable for the present embodiments are found in Kayser et al., 2006, "Principal Components Analysis of Laplacian Waveforms as a Generic Method for Identifying ERP Generator Patterns: I. Evaluation with Auditory Oddball Tasks," Clinical Neurophysiology 117(2):348; Zhang et al., 2006, "A Cortical Potential Imaging Study from Simultaneous Extra- and Intra-cranial Electrical Recordings by Means of the Finite Element Method," Neuroimage, 31(4): 1513; Perrin et al., 1987, " Scalp Current Density Mapping: Value and Estimation from Potential Data," IEEE transactions on biomedical engineering, BME-34(4):283; Ferree et al., 2000, " Theory and Calculation of the Scalp Surface Laplacian, "wwwdotcsidotuoregondotedu/members/ferree/tutorials/ Surface Laplacian; and Babiloni et al., 1997, "High resolution EEG: a new model-dependent spatial deblurring method using a realistically-shaped MR-constructed subject's head model," Electroencephalography and clinical Neurophysiology 102:69.

In any of the above embodiments, the spatial characteristics can be represented using a discrete or continuous spatial coordinate system, as desired. When the coordinate system is discrete, it typically corresponds to the locations of the measuring devices (e.g., locations on the scalp, epicortical surface, cerebral cortex or deeper in the brain). When the coordinate system is continuous, it preferably describes the approximate shape of the scalp or epicortical surface, or some sampled version thereof. A sampled surface can be represented by a point-cloud which is a set of points in a three-dimensional space, and which is sufficient for describing the topology of the surface. For a continuous coordinate system, the spatial characteristics can be obtained by piecewise interpolation between the locations of the measuring devices. The piecewise interpolation preferably utilizes a smooth analytical function or a set of smooth analytical functions over the surface.

In some embodiments of the invention the non-spatial characteristics are obtained separately for each spatial characteristic. For example, the non-spatial characteristics can be obtained separately for each channel. When the spatial characteristics are continuous, the non-spatial characteristics are preferably obtained for a set of discrete points over the continuum. Typically, this set of discrete points includes at least the points used for the piecewise interpolation, but may also include other points over the sampled version of the surface.

The non-spatial characteristics preferably include temporal characteristics, which are obtained by segmenting the data according to the time of acquisition. The segmentation results in a plurality of data segments each corresponding to an epoch over which the respective data segment was acquired. The length of the epoch depends on the temporal resolution characterizing the type f neurophysiological data. For example, for EEG or MEG data, a typical epoch length is approximately 1000 ms.

Other non-spatial characteristics can be obtained by data decomposing techniques. In various exemplary embodiments of the invention the decomposition is performed separately for each data segment of each spatial characteristic. Thus, for a particular data channel, decomposition is applied, e.g., sequentially to each data segment of this particular channel (e.g., first to the segment that corresponds to the first epoch, then to the segment that correspond to the second epoch and so on). Such sequential decomposition is performed for other channels as well.

The neurophysiological data can be decomposed by identifying a pattern of peaks in the data, or, more preferably by means of waveform analysis, such as, but not limited to, wavelet analysis. In some embodiments of the present invention the peak identification is accompanied by a definition of a spatiotemporal neighborhood of the peak. The neighborhood can be defined as a spatial region (two- or three-dimensional) in which the peak is located and/or a time-interval during which the peak occurs. Preferably, both a spatial region and time-interval are defined, so as to associate a spatiotemporal neighborhood for each peak. The advantage of defining such neighborhoods is that they provide information regarding the spreading structure of the data over time and/or space. The size of the neighborhood (in terms of the respective dimension) can be determined based on the property of the peak. For example, in some embodiments, the size of the neighborhood equals the full width at half maximum (FWHM) of the peak. Other definitions of the neighborhood are not excluded from the scope of the present invention.

The waveform analysis is preferably accompanied by filtering (e.g., bandpass filtering) such that the wave is decomposed to a plurality of overlapping sets of signal peaks which together make up the waveform. The filters themselves may optionally be overlapping.

When the neurophysiological data comprise EEG data, one or more of the following frequency bands can be employed during the filtering: delta band (typically from about 1 Hz to about 4 Hz), theta band (typically from about 3 to about 8 Hz), alpha band (typically from about 7 to about 13 Hz), low beta band (typically from about 12 to about 18 Hz), beta band (typically from about 17 to about 23 Hz), and high beta band (typically from about 22 to about 30 Hz). Higher frequency bands, such as, but not limited to, gamma band (typically from about 30 to about 80 Hz), are also contemplated.

Following the waveform analysis, waveform characteristics, such as, but not limited to, time (latency), frequency and optionally amplitude are preferably extracted. These waveform characteristics are preferably obtained as discrete values, thereby forming a vector whose components are the individual waveform characteristics. Use of discrete values is advantageous since it reduces the amount of data for further analysis. Other reduction techniques, such as, but not limited to, statistical normalization (e.g., by means of standard score, or by employing any statistical moment) are also contemplated. Normalization can be used for reducing noise and is also useful when the method is applied to data acquired from more than one subject and/or when the interfaces between the measuring device and the brain vary among different subjects or among different locations for a single subject. For example, statistical normalization can be useful when there is non-uniform impedance matching among EEG electrodes.

The extraction of characteristics results in a plurality of vectors, each of which includes, as the components of the vector, the spatial characteristics (e.g., the location of the respective electrode or other measuring device), and one or more non-spatial characteristics as obtained from the segmentation and decomposition. Each of these vectors is a feature of the data, and any pair of vectors whose characteristics obey some relation (for example, causal relation wherein the two vectors are consistent with flow of information from the location associated with one vector to the location associated with the other vector) constitutes two activity-related features.

The extracted vectors thus define a multidimensional space. For example, when the components include location, time and frequency, the vectors define a three-dimensional space, and when the components include location, time, frequency and amplitude, the vectors define a four-dimensional space. Higher number of dimensions is not excluded from the scope of the present invention.

When the analysis is applied to neurophysiological data of one subject, each feature of the data is represented as a point within the multidimensional space defined by the vectors, and each set of activity-related features is represented as a set of points such that any point of the set is within a specific distance along the time axis (also referred to hereinbelow as "latency-difference") from one or more other points in the set.

When the analysis is applied to neurophysiological data acquired from a group or sub-group of subjects, a feature of the data is preferably represented as a cluster of discrete points in the aforementioned multidimensional space. A cluster of points can also be defined when the analysis is applied to neurophysiological data of a single subject. In these embodiments, vectors of waveform characteristics are extracted separately for separate stimuli presented to the subject, thereby defining clusters of points within the multidimensional space, where each point within the cluster corresponds to a response to a stimulus applied at a different time. The separate stimuli optionally and preferably form a set of repetitive presentations of the same or similar stimulus, or a set of stimuli which are not necessarily identical but are of the same type (e.g., a set of not-necessarily identical visual stimuli). Use of different stimuli at different times is not excluded from the scope of the present invention.

Also contemplated are combinations of the above representations, wherein data are collected from a plurality of subjects and for one or more of the subjects, vectors of waveform characteristics are extracted separately for time-separated stimuli (i.e., stimuli applied at separate times). In these embodiments, a cluster contains points that correspond to different subjects as well as points that correspond to a response to a separated stimulus. Consider, for example, a case in which data were collected from 10 subjects, wherein each subject was presented with 5 stimuli during data acquisition. In this case, the dataset includes 5×10=50 data segment, each corresponding to a response of one subject to one stimulus. Thus, in a cluster within the multidimensional space may include up to 5×10 points, each representing a vector of characteristics extracted from one of the data segments.

Whether representing characteristics of a plurality of subjects and/or characteristics of a plurality of responses to stimuli presented to a single subject the width of a cluster along a given axis of the space describes a size of an activity window for the corresponding data characteristic (time, frequency, etc). As a representative example, consider the width of a cluster along the time axis. Such width is optionally and preferably used by the method to describe the latency range within which the event occurs across multiple subjects. Similarly, the width of a cluster along the frequency axis can be used for describing the frequency band indicating an occurrence of an event occurring across multiple subjects; the widths of a cluster along the location axes (e.g., two location axes for data corresponding to a 2D location map, and three location axes for data corresponding to a 3D location map) can be used to define a set of adjoining electrodes at which the event occurs across multiple subjects, and the width of a cluster along the amplitude axis can be used to define an amplitude range indicating an occurrence of event across multiple subjects.

For a group or sub-group of subjects, activity-related features can be identified as follows. A single cluster along the time axis is preferably identified as representing a unitary event occurring within a time window defined, as stated, by the width of the cluster. This window is optionally and preferably narrowed to exclude some outlier points, thereby redefining the latency range characterizing the respective data feature. For a succession of clusters along the time axis, wherein each cluster in the series has a width (along the time axis) within a particular constraint, a pattern extraction procedure is preferably implemented for identifying those clusters which obey connectivity relations thereamongst. Broadly speaking such procedure can search over the clusters for pairs of clusters in which there are connectivity relations between a sufficient number of points between the clusters.

The pattern extraction procedure can include any type of clustering procedures, including, without limitation, a density-based clustering procedure, a nearest-neighbor-based clustering procedure, and the like. A density-based clustering procedure suitable for the present embodiments is described in Cao et al., 2006, "Density-based clustering over an evolving data stream with noise," Proceedings of the Sixth SIAM International Conference on Data Mining Bethesda, Md., p. 328-39. A nearest-neighbor clustering procedure suitable for the present embodiments is described in [R. O. Duda, P. E. Hart and D. G. Stork, "Pattern Classification" (2nd Edition), A Wiley-Interscience Publication, 2000]. When nearest-neighbor clustering procedure is employed, clusters are identified and thereafter gathered to form meta-clusters based on spatiotemporal distances among the clusters. The meta-clusters are, therefore, clusters of the identified clusters. In these embodiments, the meta-clusters are the features of the data, and activity-related features are identified among the meta-clusters.

Figure 2A:
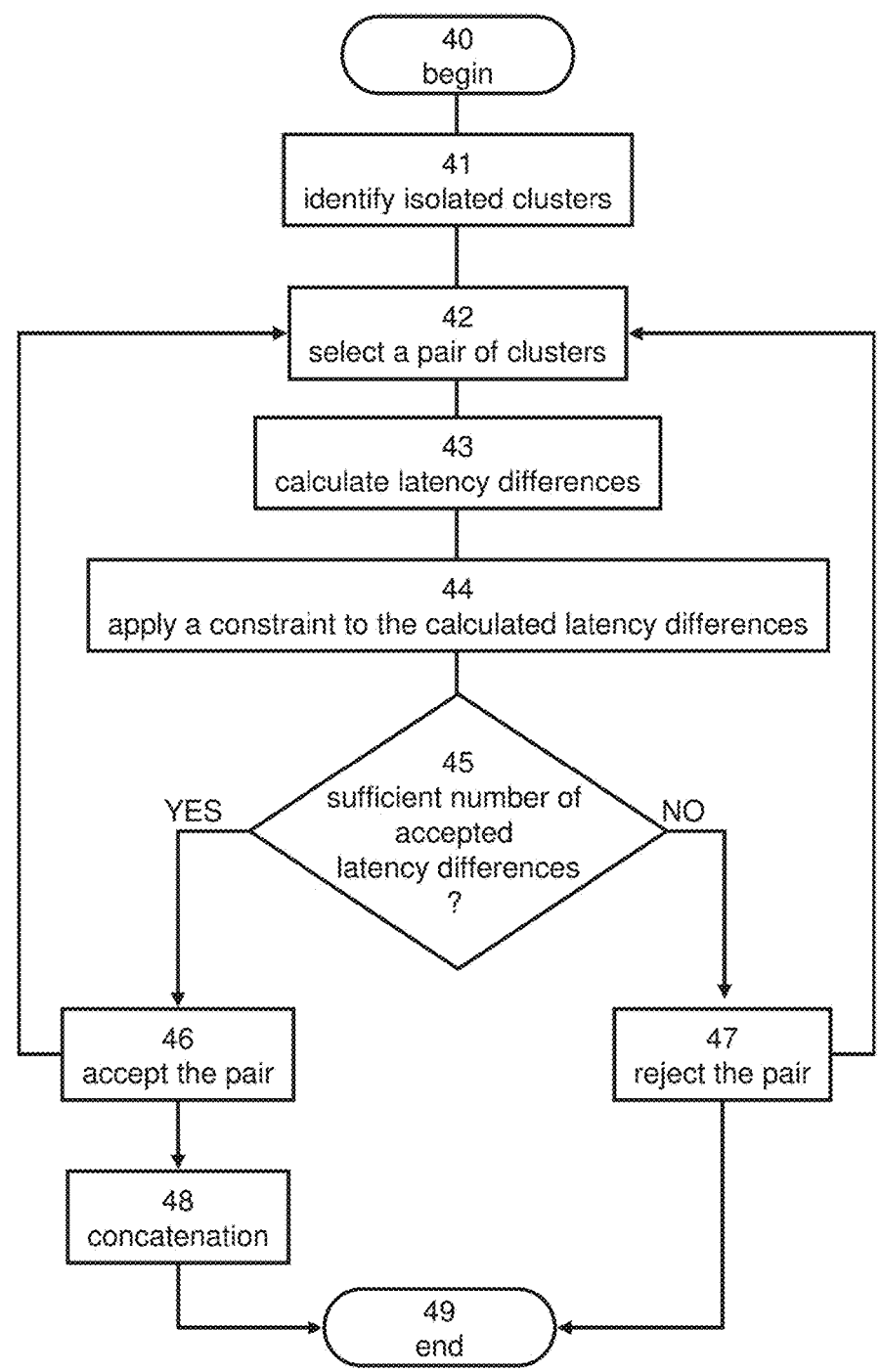

FIG. 2A is a flowchart diagram describing a procedure 12 for identifying activity-related features for a group of subjects, according to some embodiments of the present invention. Procedure 12 begins at 40 and continues to 41 at which isolated clusters are identified. The present embodiments contemplate both subspace clustering, wherein clusters are identified on a particular projection of the multidimensional space, and full-space clustering wherein clusters are identified on the entire multidimensional space. Subspace clustering is preferred from the standpoint of computation time, and full-space clustering is preferred from the standpoint of features generality.

One representative example of subspace clustering includes identification of clusters along the time axis, separately for each predetermined frequency band and each predetermined spatial location. The identification optionally and preferably features a moving time-window with a fixed and predetermined window width. A typical window width for EEG data is about 200 ms for the delta band. A restriction on a minimal number of points in a cluster is optionally applied so as not to exclude small clusters from the analysis. Typically cluster with less than X points, where X equals about 80% of the subjects in the group, are excluded. The minimal number of points can be updated during the procedure. Once an initial set of clusters is defined, the width of the time window is preferably lowered.

Another representative example of subspace clustering includes identification of clusters over a space-time subspace, preferably separately for each predetermined frequency band. In this embodiment, the extracted spatial characteristics are represented using a continuous spatial coordinate system, e.g., by piecewise interpolation between the locations of the measuring devices, as further detailed hereinabove. Thus, each cluster is associated with a time window as well as a spatial region, wherein the spatial region may or may not be centered at a location of a measuring device. In some embodiments, at least one cluster is associated with a spatial region which is centered at a location other than a location of a measuring device. The space-time subspace is typically three-dimensional with one temporal dimension and two spatial dimensions, wherein each cluster is associated with a time-window and a two-dimensional spatial region over a surface which may correspond, e.g., to the shape of the scalp surface, the epicortical surface and the like. Also contemplated is a four-dimensional space-time space wherein each cluster is associated with a time-window and a three-dimensional spatial region over a volume corresponding, at least in part, to internal brain.

Another representative example of subspace clustering includes identification of clusters over a frequency-space-time subspace. In this embodiment, instead of searching for clusters separately for each predetermined frequency band, the method allows identification of clusters also at frequencies which are not predetermined. Thus, the frequency is considered as a continuous coordinate over the subspace. As in the embodiment of space-time subspace, the extracted spatial characteristics are represented using a continuous spatial coordinate system. Thus, each cluster is associated with a time window, a spatial region and a frequency band. The spatial region can be two- or three-dimensional as further detailed hereinabove. In some embodiments, at least one cluster is associated with a spatial region which is centered at a location other than a location of a measuring device, and at least one cluster is associated with a frequency band which includes frequencies of two or more of the delta, theta, alpha, low beta, beta, high beta and gamma bands. For example, a cluster can be associated with a frequency band spanning over part of the delta band and part of the theta band, or part of the theta band and part of the alpha band, or part of the alpha band and part of the low beta band, etc.

Procedure 12 optionally and preferably continues to 42 at which, a pair of clusters is selected. The procedure optionally and preferably continues to 43 at which, for each subject that is represented in the selected pair, latency difference (including zero difference) between the corresponding events is optionally calculated. The procedure continues to 44 at which a constraint is applied to the calculated latency differences such that latency differences which are outside a predetermined threshold range (e.g., 0-30 ms) are rejected while latency differences which are within the predetermined threshold range are accepted. The procedure continues to decision 45 at which the procedure determines whether the number of accepted differences is sufficiently large (i.e., above some number, e.g., above 80% of the subjects in the group). If the number of accepted differences is not sufficiently large the procedure proceeds to 46 at which the procedure accepts the pair of clusters and identifies it as a pair of activity-related features. If the number of accepted differences is sufficiently large the procedure proceeds to 47 at which the procedure reject the pair. From 46 or 47 the procedure of the present embodiments loops back to 42.

An illustrative example for determining relations among the data features and identification of activity-related features is shown in FIG. 2B. The illustration is provided in terms of a projection onto a two-dimensional space which includes time and location. The present example is for an embodiment in which the spatial characteristics are discrete, wherein the identification of clusters is along the time axis, separately for each predetermined frequency band and each predetermined spatial location. The skilled person would know how to adapt the description for the other dimensions, e.g., frequency, amplitude, etc. FIG. 2B illustrates a scenario in which data are collected from 6 subjects (or from a single subject, present with 6 stimuli at different times), enumerated 1 through 6. For clarity of presentation, different data segments data (e.g., data collected from different subjects, or from the same subject but for stimuli of different times) are separated along a vertical axis denoted "Data Segment No." For each segment, an open circle represents an event recorded at one particular location (by means of a measuring device, e.g., EEG electrode) denoted "A", and a solid disk represents an event recorded at another particular location denoted "B".

The time axis represents the latency of the respective event, as measured, e.g., from a time at which the subject was presented with a stimulus. The latencies of the events are denoted herein $t^{(i)}_A$ and $t^{(i)}_B$, where i represents the segment index (i=1, . . . , 6) and A and B represent the location. For clarity of presentation, the latencies are not shown in FIG. 2B, but one of ordinary skills in the art, provided with the details described herein would know how to add the latencies to the drawing.

For each of locations A and B, a time window is defined. These time windows, denoted $\Delta t_A$ and $\Delta t_B$, correspond to the width of the clusters along the time axis and they can be the same or different from one another, as desired. Also defined is a latency difference window $\Delta t_{AB}$, between the two unitary events. This window corresponds to the separation along the time axis between the clusters (e.g., between their centers). The window $\Delta t_{AB}$ is illustrated as an interval having a dashed segment and a solid segment. The length of the dashed segment represents the lower bound of the window and the overall length of the interval represents the upper bound of the window. $\Delta t_A$, $\Delta t_B$ and $\Delta t_{AB}$ are part of the criteria for determining whether to accept the pair of events recorded at A and B as activity-related features.

The time windows $\Delta t_A$ and $\Delta t_B$ are preferably used for identifying unitary events in the group. As shown, for each of segment Nos. 1, 2, 4 and 5 both events fall within the respective time windows (mathematically, this can be written as follows: $t^{(i)}_A \in \Delta t_A$, $t^{(i)}_B \in \Delta t_A$, i=1, 2, 4, 5). On the other hand, for segment No. 3 the event recorded at A falls outside $\Delta t_A$ ($t^{(3)}_A \notin \Delta t_A$) while the event recoded at B falls within $\Delta t_B$ ($t^{(3)}_B \in \Delta t_B$), and for segment No. 6 the event recorded at A falls within $\Delta t_A$ ($t^{(6)}_A \in \Delta t_A$) while the event recoded at B falls outside $\Delta t_B$ ($t^{(6)}_B \notin \Delta t_B$). Thus, for location A, a unitary event is defined as a cluster of data points obtained from segment Nos. 1, 2, 4, 5 and 6, and for location B, a unitary event is defined as a cluster of data points obtained from segment Nos. 1-5.

The latency difference window $\Delta t_{AB}$ is preferably used for identifying activity-related features. In various exemplary embodiments of the invention the latency difference $\Delta t^{(i)}{}_{AB}$ (i=1, 2, . . . , 5) of each segment is compared to the latency difference window $\Delta t_{AB}$. In various exemplary embodiments of the invention a pair of features is accepted as an activity-related pair if (i) each of the features in the pair belongs to a unitary event, and (ii) the corresponding latency difference falls within $\Delta t_{AB}$. In the illustration of FIG. 2B, each of the pairs recorded from segment Nos. 4 and 5 is accepted as a pair of activity-related features, since both criteria are met for each of those segment ($\Delta t^{(i)}{}_{AB} \in \Delta t_{AB}$, $t^{(i)}{}_A \in \Delta t_A$, $t^{(i)}{}_B \in \Delta t_A$, i=4, 5). The pairs recorded from segment Nos. 1-3 do not pass the latency difference criterion since each of $\Delta t^{(1)}{}_{AB}$, $\Delta t^{(2)}{}_{AB}$ and $\Delta t^{(3)}{}_{AB}$ is outside $\Delta t_{AB}$ ($\Delta t^{(i)}{}_{AB} \notin \Delta t_{AB}$, i=1, 2, 3). These pairs are, therefore, rejected. Notice that in the present embodiment, even though the pair obtained from segment No. 6 passes the latency difference criterion, the pair is rejected since it fails to pass the time-window criterion ($\Delta t^{(6)}{}_{AB} \notin \Delta t_{AB}$).

In various exemplary embodiments of the invention the procedure also accepts pairs corresponding to simultaneous events of the data that occur at two or more different locations. Although such events are not causal with respect to each other (since there is no flow of information between the locations), the corresponding features are marked by the method. Without being bounded to any particular theory, the present inventors consider that simultaneous events of the data are causally related to another event, although not identified by the method. For example, the same physical stimulus can generate simultaneous events in two or more locations in the brain.

The identified pairs of activity-related features, as accepted at 46, can be treated as elementary patterns which can be used as elementary building blocks for constructing complex patterns within the feature space. In various exemplary embodiments of the invention, the method proceeds to 48 at which two or more pairs of activity-related features are joined (e.g., concatenated) to form a pattern of more than two features. The criterion for the concatenation can be similarity between the characteristics of the pairs, as manifested by the vectors. For example, in some embodiments, two pairs of activity-related features are concatenated if they have a common feature. Symbolically, this can be formulated as follows: the pairs "A-B" and "B-C" have "B" as a common feature and are concatenated to form a complex pattern A-B-C.

Preferably, the concatenated set of features is subjected to a thresholding procedure, for example, when X % or more of the subjects in the group are included in the concatenated set, the set is accepted, and when less than X % of the subjects in the group are included in the concatenated set, the set is rejected. A typical value for the threshold X is about 80.

Each pattern of three or more features thus corresponds to a collection of clusters defined such that any cluster of the collection is within a specific latency-difference from one or more other clusters in the collection. Once all pairs of clusters are analyzed procedure 12 continues to terminator 49 at which it ends.

Referring again to FIG. 1, at 13 a subject-specific brain network activity (BNA) pattern is constructed. Before providing a further detailed description of the method, the general concept of BNA patterns will be explained.

FIG. 3 is a representative example of a BNA pattern 20 which may be extracted from neurophysiological data, according to some embodiments of the present invention. BNA pattern 20 has a plurality of nodes 22, each representing one of the activity-related features. For example, a node can represent a particular frequency band (optionally two or more particular frequency bands) at a particular location and within a particular time-window or latency range, optionally with a particular range of amplitudes.

Some of nodes 22 are connected by edges 24 each representing the causal relation between the nodes at the ends of the respective edge. Thus, the BNA pattern is represented as a graph having nodes and edges. In various exemplary embodiments of the invention the BNA pattern includes plurality of discrete nodes, wherein information pertaining to features of the data is represented only by the nodes and information pertaining to relations among the features is represented only by the edges.

FIG. 3 illustrates BNA pattern 20 within a template 26 of a scalp, allowing relating the location of the nodes to the various lobes of the brain (frontal 28, central 30, parietal 32, occipital 34 and temporal 36). The nodes in the BNA pattern can be labeled by their various characteristics. A color coding or shape coding visualization technique can also be employed, if desired. For example, nodes corresponding to a particular frequency band can be displayed using one color or shape and nodes corresponding to another frequency band can be displayed using another color or shape. In the representative example of FIG. 3, two colors are presented. Red nodes correspond to Delta waves and green nodes correspond to Theta waves.

A BNA pattern, such as the illustrated pattern 20, can describe brain activity of a single subject or a group or sub-group of subjects. A BNA pattern which describes the brain activity of a single subject is referred to herein as a subject-specific BNA pattern, and BNA pattern which describes the brain activity of a group or sub-group of subjects is referred to herein as a group BNA pattern.

When BNA pattern 20 is a subject-specific BNA pattern, only vectors extracted from data of the respective subject are used to construct the BNA pattern. Thus, each node corresponds to a point in the multidimensional space and therefore represents an activity event in the brain. When BNA pattern 20 is a group BNA pattern, some nodes can correspond to a cluster of points in the multidimensional space and therefore represents an activity event which is prevalent in the group or sub-group of subjects. Due to the statistical nature of a group BNA pattern, the number of nodes (referred to herein as the "order") and/or edges (referred to herein as the "size") in a group BNA pattern is typically, but not necessarily, larger than the order and/or size of a subject-specific BNA pattern.

As a simple example for constructing a group BNA pattern, the simplified scenario illustrated in FIG. 2B is considered, wherein a "segment" corresponds to a different subject in a group or sub-group of subjects. The group data include, in the present example, two unitary events associated with locations A and B. Each of these events forms a cluster in the multidimensional space. In various exemplary embodiments of the invention each of the clusters, referred to herein as clusters A and B, is represented by a node in the group BNA. The two clusters A and B are identified as activity-related features since there are some individual points within these clusters that pass the criteria for such relation (the pairs of Subject Nos. 4 and 5, in the present example). Thus, in various exemplary embodiments of the invention the nodes corresponding to clusters A and B are connected by an edge. A simplified illustration of the resulting group BNA pattern is illustrated in FIG. 2C.

Since the group BNA pattern describes brain activity in several subjects, it is typically constructed for a group or sub-group of subjects with some common classification which may pertain to condition, characteristics, affiliation and the like. Such group BNA patterns can be annotated according to the group classification.

Herein, the term "annotated BNA pattern" will be used to denote a BNA pattern that is associated with annotation information. The annotation information can be stored separately from the BNA pattern (e.g., in a separate file on a computer readable medium). The annotation information is preferably global annotation wherein the entire BNA pattern is identified as corresponding to a specific brain related disorder or condition. Thus, for example, the annotation information can pertain to the presence, absence or level of the specific disorder or condition. Also contemplated are embodiments in which the annotation information pertains to a specific brain related disorder or condition in relation to a treatment applied to the subject. For example, a BNA pattern can be annotated as corresponding to a treated brain related disorder. Such BNA pattern can also be annotated with the characteristics of the treatment, including dosage, duration, and elapsed time following the treatment. A BNA pattern can optionally and preferably be annotated as corresponding to an untreated brain related disorder.

As used herein, the term "treatment" includes abrogating, substantially inhibiting, slowing or reversing the progression of a condition, substantially ameliorating clinical or aesthetical symptoms of a condition or substantially preventing the appearance of clinical or aesthetical symptoms of a condition. Treatment can include any type of intervention, both invasive and noninvasive, including, without limitation, pharmacological, surgical, irradiative, rehabilitative, and the like.

Alternatively or additionally, the BNA pattern can be identified as corresponding to a specific group of individuals (e.g., a specific gender, ethnic origin, age group, etc.), wherein the annotation information pertains to the characteristics of this group of individuals. In some embodiments of the present invention the annotation information includes local annotation wherein nodes at several locations over the BNA pattern are identified as indicative of specific disorder, condition and/or group.

Unlike the group BNA pattern, the nodes in the subject-specific BNA pattern are all based on vectors extracted from data of the respective subject. A subject-specific BNA pattern is optionally and preferably constructed by comparing the features and relations among features of the data collected from the respective subject to the features and relations among features of reference data. The reference data can include group data and/or data of a single subject, preferably the same subject under analysis, and/or synthetic data generated, e.g., by means of a neurophysiological model.

When the reference data comprise group data, points and relations among points associated with the subject's data are compared to clusters and relations among clusters associated with the group's data. Consider, for example, the simplified scenario illustrated in FIG. 2B, wherein a "segment" corresponds to a different subject in a group or sub-group of subjects. Cluster A does not include a contribution from Subject No. 3, and cluster B does not include a contribution from Subject No. 6, since for these subjects the respective points fail to pass the time-window criterion. Thus, in various exemplary embodiments of the invention when a subject-specific BNA pattern is constructed for Subject No. 3 it does not include a node corresponding to location A, and when a subject-specific BNA pattern is constructed for Subject No. 6 it does not include a node corresponding to location B. On the other hand, both locations A and B are represented to as nodes in the subject-specific BNA patterns constructed for any of Subject Nos. 1, 2, 4 and 5.

For those subjects for which the respective points are accepted as a pair of activity-related features (Subject Nos. 4 and 5, in the present example), the corresponding nodes are preferably connected by an edge. A simplified illustration of a subject-specific BNA pattern for such a case is shown in FIG. 2D.

Note that for this simplified example of only two nodes, the subject-specific BNA of FIG. 2D is similar to the group BNA of FIG. 2C. For a larger number of nodes, the order and/or size of the group BNA pattern is, as stated, typically larger than the order and/or size of the subject-specific BNA pattern. An additional difference between the subject-specific and group BNA patterns can be manifested by the degree of relation between the activity-related features represented by the edges, as further detailed hereinbelow.

For subjects for which the respective points were rejected (Subject Nos. 1 and 2, in the present example), the corresponding nodes are preferably not connected by an edge. A simplified illustration of a subject-specific BNA pattern for such case is shown in FIG. 2E.

When the reference data include data of a single subject, vectors of waveform characteristics are extracted separately for time-separated stimuli, to define clusters of points where each point within the cluster corresponds to a response to a stimulus applied at a different time, as further detailed hereinabove. The procedure for constructing subject-specific BNA pattern in these embodiments is preferably the same as procedure for constructing a group BNA pattern described above. However, since all data are collected from a single subject, the BNA pattern is subject-specific.

Thus, the present embodiments contemplate two types of subject-specific BNA patterns: a first type that describes the association of the particular subject to a group or sub-group of subjects, which is a manifestation of a group BNA pattern for the specific subject, and a second type that describes the data of the particular subject without associating the subject to a group or sub-group of subjects. The former type of BNA pattern is referred to herein as an associated subject-specific BNA pattern, and the latter type of BNA pattern is referred to herein as an unassociated subject-specific BNA to pattern.

For unassociated subject-specific BNA pattern, the analysis is preferably performed on the set of repetitive presentations of a single stimulus, namely on a set of single trials, optionally and preferably before averaging the data and turning it to one single vector of the data. For group BNA patterns, on the other hand, the data of each subject of the group is optionally and preferably averaged and thereafter turned into vectors of the data.

Note that while the unassociated subject-specific BNA pattern is generally unique for a particular subject (at the time the subject-specific BNA pattern is constructed), the same subject may be characterized by more than one associated subject-specific BNA patterns, since a subject may have different associations to different groups. Consider for example a group of healthy subjects and a group of non-healthy subjects all suffering from the same brain disorder. Consider further a subject Y which may or may not belong to one of those groups. The present embodiments contemplate several subject-specific BNA patterns for subject Y. A first BNA pattern is an unassociated subject-specific BNA pattern, which, as stated is generally unique for this subject, since it is constructed from data collected only from subject Y. A second BNA pattern is an associated subject-specific BNA pattern constructed in terms of the relation between the data of a subject Y to the data of the healthy group. A third BNA pattern is an associated subject-specific BNA pattern constructed in terms of the relation between the data of a subject Y to the data of the non-healthy group. Each of these BNA patterns are useful for assessing the condition of subject Y. The first BNA pattern can be useful, for example, for monitoring changes in the brain function of the subject over time (e.g., monitoring brain plasticity or the like) since it allows comparing the BNA pattern to a previously constructed unassociated subject-specific BNA pattern. The second and third BNA pattern can be useful for determining the level of association between subject Y and the respective group, thereby determining the likelihood of brain disorder for the subject.

Also contemplated are embodiments in which the reference data used for constructing the subject-specific BNA pattern corresponds to history data previously acquired from the same subject. These embodiments are similar to the embodiments described above regarding the associated subject-specific BNA pattern, except that the BNA pattern is associated to the history of the same subject instead of to a group of subjects.

Additionally contemplated are embodiments in which the reference data corresponds to data acquired from the same subject at some later time. These embodiments allow investigating whether data acquired at an early time evolve into the data acquired at the later time. A particular and non limiting example is the case of several treatment sessions, e.g., N sessions, for the same subject. Data acquired in the first several treatment sessions (e.g., from session 1 to session $k_1 < N$) can be used as reference data for constructing a first associated subject-specific BNA pattern corresponding to mid sessions (e.g., from session $k_2 > k_1$ to session $k_3 > k_2$), and data acquired in the last several treatment sessions (e.g., from session $k_4$ to session N) can be used as reference data for constructing a second associated subject-specific BNA pattern corresponding to the aforementioned mid sessions, where $1 < k_1 < k_2 < k_3 < k_4$. Such two associated subject-specific BNA patterns for the same subject can be used for determining data evolution from the early stages of the treatment to the late stages of the treatment.

Further contemplated are embodiments in which the reference data comprise data synthesized from a neurophysiological model. The model can be based on prior knowledge regarding expected spatiotemporal flow patterns among various functional regions in the brain for a particular condition of the brain.

A neurophysiological model can be constructed by processing training neurophysiological data, collected from a sufficiently large sample size, and employing statistical analysis and/or machine learning techniques to construct a predictive model. The sources of the training neurophysiological data can be of any type that provides information regarding neurological activity in the brain. Representative examples include, without limitation, EEG data, MEG data, CAT data, PET data, MRI data, fMRI data, ultrasound data, SPECT data, BCI data, and data from neuroprostheses at the neural level. Optionally, the model is constructed based on combination of two or more different types of data. The training set can also include literature data.

The training set may optionally be compiled from subjects from the different research groups, including, without limitation, at least one control group and at least one target group of subjects with similar behaviors, e.g., pathological actions or activities performed in a specific way due to a pathological condition, or non-pathological actions which the subjects are requested to perform. A technique for generating a neurophysiological model suitable for some embodiments of the present invention is found in International Publication No. WO2009/069135, assigned to the same assignee as the present application and being incorporated by reference by its entirety.

Several models that are able to fit the training set can be constructed, and scored, e.g., by a likelihood rating, reflecting the likelihood of the model fitting the training set. The model or models that have the highest scores can be selected and used a computerized engine for generating synthetic neurophysiological data to be used as the reference data.

In various exemplary embodiments of the invention the selected model(s) receives input regarding the subject under investigation and generate in response synthetic neurophysiological data which are expected to be obtained from such a subject. The selected model optionally and preferably receives input pertaining to a classification group to which the subject is expected to belong, and also a request regarding the type of synthetic data which is required as a reference.

As a representative example, consider a subject under analysis that is frequently engaged in a contact sport activity. Suppose that it is desired to construct a subject-specific BNA which is associated with brain concussion. In this exemplified situation, the selected model preferably receive input regarding the classification group to which the subject belong (e.g., age, gender, and type of sport) as well as a request for generating synthetic data which are characteristic for a condition of brain concussion for the particular classification group. The synthetic data generated by the neurophysiological is used by the method of the present embodiments as reference data for constructing the associated subject-specific BNA. As stated, the same subject can have more than one associated subject-specific BNA. Thus, the model can additionally receive, for example, input regarding the classification group together with a request to generate synthetic data which are characteristic for normal brain function, thus concussion for the particular classification group. The latter synthetic data can be used by the method of the present embodiments as reference data for constructing a subject-specific BNA associated with normal brain function.

Each pair of nodes (or equivalently each edge) in the constructed BNA pattern is optionally and preferably assigned with a connectivity weight pattern, thereby providing a weighted BNA pattern. The connectivity weight is represented in FIGS. 2C and 2D and 3 by the thickness of the edges connecting two nodes. For example, thicker edges can correspond to higher weights and thinner edges can correspond to lower weights.

In various exemplary embodiments of the invention the connectivity weight comprises a weight index WI calculated based on at least one of the following cluster properties: (i) the number of subjects participating in the corresponding cluster pair, wherein greater weights are assigned for larger number of subjects; (ii) the difference between the number of subjects in each cluster of the pair (referred to as the "differentiation level" of the pair), wherein greater weights are assigned for lower differentiation levels; (iii) the width of the time windows associated with each of the corresponding clusters (see, e.g., $\Delta t_A$ and $\Delta t_B$ in FIG. 2A), wherein greater weights are assigned for narrower windows; (iv) the latency difference between the two clusters (see $\Delta t_{AB}$ in FIG.

2A), wherein greater weights are assigned for narrower windows; (v) the amplitude of the signal associated with the corresponding clusters; (vi) the frequency of the signal associated with the corresponding clusters; and (vii) the width of a spatial window defining the cluster (in embodiments in which the coordinate system is continuous). For any of the cluster properties, except properties (i) and (ii), one or more statistical observables of the property, such as, but not limited to, average, median, supremum, infimum and variance over the cluster are preferably used.

For a group BNA pattern or an unassociated subject-specific BNA pattern, the connectivity weight preferably equals the weight index WI as calculated based on the cluster properties.

For an associated subject-specific BNA pattern, the connectivity weight of a pair of nodes is preferably assigned based on the weight index WI as well as one or more subject-specific and pair-specific quantities denoted SI. Representative examples of such quantities are provided below.

In various exemplary embodiments of the invention a pair of nodes of the associated subject-specific BNA pattern is assigned with a connectivity weight which is calculated by combining WI with SI. For example, the connectivity weight of a pair in the associated subject-specific BNA pattern can be given by WI·SI. When more than one quantities (say N quantities) are calculated for a given pair of nodes, the pair can be assigned with more than one connectivity weights, e.g., WI·SI$_1$, WI·SI$_2$, ..., WI·SI$_N$, wherein SI$_1$, SI$_2$, ..., SI$_N$, are N calculated quantities. Alternatively or additionally, all connectivity weights of a given pair can be combined, e.g., by averaging, multiplying and the like.

The quantity SI can be, for example, a statistical score characterizing the relation between the subject-specific pair and the corresponding clusters. The statistical score can be of any type, including, without limitation, deviation from average, absolute deviation, standard-score and the like. The relation for whom the statistical score is calculated can pertain to one or more properties used for calculating the weight index WI, including, without limitation, latency, latency difference, amplitude, frequency and the like.

A statistical score pertaining to latency or latency difference is referred to herein as a synchronization score and denoted SIs. Thus, a synchronization score according to some embodiments of the present invention can be obtained by calculating a statistical score for (i) the latency of the point as obtained for the subject (e.g., $t^{(i)}_A$ and $t^{(i)}_B$, in the above example) relative to the group-average latency of the corresponding cluster, and/or (ii) the latency difference between two points as obtained for the subject (e.g., $\Delta t^{(i)}_{AB}$), relative to the group-average latency difference between the two corresponding clusters.

A statistical score pertaining to amplitude is referred to herein as an amplitude score and denoted SIa. Thus an amplitude score according to some embodiments of the present invention is obtained by calculating a statistical score for the amplitude as obtained for the subject relative to the group-average amplitude of the corresponding cluster.

A statistical score pertaining to frequency is referred to herein as a frequency score and denoted SIf. Thus a frequency score according to some embodiments of the present invention is obtained by calculating a statistical score for the frequency as obtained for the subject relative to the group-average frequency of the corresponding cluster.

A statistical score pertaining to the location is referred to herein as a location score and denoted SIl. These embodiments are particularly useful in embodiments in which a continuous coordinate system is employed, as further detailed hereinabove. Thus a location score according to some embodiments of the present invention is obtained by calculating a statistical score for the location as obtained for the subject relative to the group-average location of the corresponding cluster.

Calculation of statistical scores pertaining to other properties is not excluded from the scope of the present invention.

Following is a description of a technique for calculating the quantity SI, according to some embodiments of the present invention.

When SI is a synchronization score SIs the calculation is optionally and preferably based on the discrete time points matching the spatiotemporal constraints set by the electrode pair (Time$_{subj}$), if such exist. In these embodiments, the times of these points can are compared to the mean and standard deviation of the times of the discrete points participating in the group pattern (Time$_{pat}$), for each region to provide a regional synchronization score SIs$_r$. The synchronization score SIs is can then be calculated, for example, by averaging the regional synchronization scores of the two regions in the pair. Formally, this procedure can be written as:

$$SIs_r = 0.5 + \frac{std(Time_{pat})}{2*(abs(\overline{Time_{pat}} - T_{subj}) + std(Time_{pat}))};$$

$$SIs = \frac{1}{r}\sum SIs_r$$

An amplitude score SIa, is optionally and preferably calculated in a similar manner. Initially the amplitude of the discrete points of the individual subject (Amp$_{subj}$) is compared to the mean and standard deviation of the amplitudes of the discrete points participating in the group pattern (Amp$_{pat}$), for each region to provide a regional amplitude score SIa$_r$. The amplitude score can then be calculated, for example, by averaging the regional amplitude scores of the two regions in the pair:

$$SIa_r = 0.5 + \frac{std(Amp_{pat})}{2*(abs(\overline{Amp_{pat}} - Amp_{subj}) + std(Amp_{pat}))};$$

$$SIa = \frac{1}{r}\sum SIa_r$$

One or more BNA pattern similarities S can then be calculated as a weighted average over the nodes of the BNA pattern, as follows:

$$Ss = \frac{\sum_i (W_i * SIs_i)}{\sum_i W_i}$$

$$Sa = \frac{\sum_i (W_i * SIa_i)}{\sum_i W_i}$$

$$Sf = \frac{\sum_i (W_i * SIf_i)}{\sum_i W_i}$$

$$SI = \frac{\sum_i (W_i * SIl_i)}{\sum_i W_i}$$

Formally, an additional similarity, Sc, can be calculated, as follows:

$$Ic = \frac{\sum_i (W_i * SIc_i)}{\sum_i W_i},$$

where $SIc_i$ is a binary quantity which equals 1 if pair i exists in the subject's data and 0 otherwise.

In some embodiments of the present invention the quantity SI comprises a correlation value between recorded activities. In some embodiments, the correlation value describes correlation between the activities recorded for the specific subject at the two locations associated with the pair, and in some embodiments the correlation value describes correlation between the activities recorded for the specific subject at any of the locations associated with the pair and the group activities as recorded at the same location. In some embodiments, the correlation value describes causality relations between activities.

Procedures for calculating correlation values, such as causality relations, are known in the art. In some embodiments of the present invention the Granger theory is employed [Granger C W J, 1969, "Investigating Causal Relations By Econometric Models And Cross-Spectral Methods," Econometrica, 37(3):242]. Other techniques suitable for the present embodiments are found in Durka et al., 2001, "Time-frequency microstructure of event-related electroencephalogram desynchronisation and synchronisation," Medical & Biological Engineering & Computing, 39:315; Smith Bassett et al., 2006, "Small-World Brain Networks" Neuroscientist, 12:512; He et al., 2007, "Small-World Anatomical Networks in the Human Brain Revealed by Cortical Thickness from MRI," Cerebral Cortex 17:2407; and De Vico Fallani et al., "Extracting Information from Cortical Connectivity Patterns Estimated from High Resolution EEG Recordings: A Theoretical Graph Approach," Brain Topogr 19:125; the contents of all of which are hereby incorporated by reference.

The connectivity weights assigned over the BNA pattern can be calculated as a continuous variable (e.g., using a function having a continuous range), or as a discrete variable (e.g., using a function having a discrete range or using a lookup table). In any case, connectivity weights can have more than two possible values. Thus, according to various exemplary embodiments of the present invention the weighted BNA pattern has at least three, or at least four, or at least five, or at least six edges, each of which being assigned with a different connectivity weight.

Once the subject-specific BNA pattern is constructed it can be transmitted to a display device such as a computer monitor, or a printer. Alternatively or additionally, the BNA pattern can be transmitted to a computer-readable medium.

Referring again to FIG. 1, the method proceeds to 14 at which the subject-specific BNA pattern (e.g., pattern 20) is compared to a baseline BNA pattern which is specific to the same subject. The baseline BNA pattern can be a pattern constructed for the same subjects at a different time for example, an earlier time. Preferably, both the BNA that is constructed at 13 and the baseline BNA describe the association of the particular subject (albeit at different times) to the same group or sub-group of subjects. In various exemplary embodiments of the invention both the constructed and the baseline BNA patterns are subject-specific BNA patterns associated with brain concussion. Alternatively, both the constructed and the baseline BNA patterns can be subject-specific BNA patterns associated with normal brain function.

In some embodiments of the present invention the method loops back to 12 or 13 so that two or more subject-specific BNA patterns are eventually constructed. These embodiments allow exploiting more than one association. Thus, each subject-specific BNA is constructed based on different reference data or model but using the same neurophysiological data of the subject, and each subject-specific BNA is compared to a different baseline BNA is associated with a different brain condition.

In a representative embodiment of the present invention, the method constructs a first associated subject-specific BNA pattern which is associated with brain concussion, and a second subject-specific BNA pattern which is associated with normal brain function. Each of the constructed BNA pattern is compared to a respective baseline BNA pattern. Specifically, the first BNA pattern is compared to a baseline BNA pattern associated with brain concussion, and the second BNA pattern is compared to a baseline BNA pattern associated with normal brain function.

The comparison between BNA patterns, according to some embodiments of the present invention is preferably quantitative. In these embodiments the comparison between the BNA patterns comprises calculating BNA pattern similarity. The BNA pattern similarity is optionally and preferably calculated based on the values of the connectivity weights of the BNA patterns. For example, BNA pattern similarity can be obtained by averaging the connectivity weights over the subject-specific BNA pattern. When more than one type of connectivity weight is assigned for each pair of nodes in BNA pattern 20, the averaging is preferably performed over the BNA pattern separately for each type of connectivity weight. Optionally and preferably one or more of the averages can be combined (e.g., summed, multiplied, averaged, etc.) to provide a combined BNA pattern similarity. Alternatively, a representative of the averages (e.g., the largest) can be defined as the BNA pattern similarity.

The similarity can be expressed as a continuous or discrete variable. In various exemplary embodiments of the invention the similarity is a non-binary number. In other words, rather than determining whether the two BNA patterns are similar or dissimilar, the method calculates the degree by which the two BNA patterns are similar or dissimilar. For example, the similarity can be expressed as percentage, as a non-integer number between 0 and 1 (e.g., 0 corresponding to complete dissimilarity and 1 corresponding to comparison between a BNA pattern and itself), and the like.

In embodiments in which several subject-specific BNA patterns are obtained for the same subject, each of the subject-specific BNA patterns are preferably compared to the corresponding baseline BNA pattern. The method optionally and preferably selects the pair of BNA patterns which best match each other. Optionally, the method can assign a score to each pair of BNA patterns being compared. Such score can be, for example, one or more BNA pattern similarity S, as further detailed hereinabove. Thus, in various exemplary embodiments of the invention 52 includes calculation of at least one BNA pattern similarity S, describing the similarity between BNA pattern 20 and the baseline BNA pattern.

The BNA pattern similarity can be used as a classification score which describes, quantitatively, the membership level of the subject to the respective group. This embodiment is particularly useful when more than one subject-specific BNA patterns are constructed for the same subject using different group data, wherein the classification score can be used to assess the membership level of the subject to each of the groups. Thus, each contracted subject-specific BNA pattern can be compared to a group BNA pattern in addition or as an alternative to the comparison to the respective subject-specific baseline BNA pattern.

The method continues to 15 at which the likelihood of brain concussion is assessed responsively to the calculated similarity. For example, a concussion index can be calculated based, at least in part, on the obtained similarity. The concussion index can be the similarity itself or it can be calculated based on the similarity. For example, when high level of similarity is found between BNA patterns associated with brain concussion, the method can issue a report that there is a high likelihood that the subject has brain concussion.

When the comparison is both between BNA pattern associated with concussion and between BNA patterns associated with normal brain function, both similarity levels can be used for the assessment. For example, denoting the respective similarity levels by $S_{concussion}$ and $S_{normal}$, where both $S_{abnormal}$ and $S_{normal}$ are between 0 and 1, the concussion index $I_{concussion}$ can be calculated as:

$$I_{concussion}=(S_{concussion}+(1-S_{normal}))/2.$$

Variations of the above formula are not excluded from the scope of the present invention.

Once the likelihood is assessed, it can be transmitted to a computer-readable medium or a display device or a printing device, as desired. For example, the concussion index can be presented to the user graphically on a scale-bar. A representative example of such graphical presentation is shown in FIG. 4.

The similarity level can optionally and preferably also be used as a prognosis indicator for the particular subject. In particular, observing the change in similarity level over time can be used as a prognosis indicator. For example, when the level of similarity to the normal baseline increases with time, the rate of increment can be used as a prognosis indicator.

Thus, the method optionally and preferably extracts 16 prognosis information responsively to the calculated similarity. The baseline BNA pattern can also be associated with annotation information pertaining to a treatment, optionally and preferably together with the characteristics of the treatment, e.g., dosage, duration, and elapsed time following the treatment. A comparison of the constructed BNA pattern to such type of baseline BNA patterns, can provide information regarding the responsiveness of the subject to treatment and/or the efficiency of the treatment for that particular subject. Such comparison can optionally and preferably be used for extracting prognostic information in connection to the specific treatment. A BNA pattern that is complementary to such baseline BNA pattern is a BNA pattern that is annotated as corresponding to an untreated brain related disorder. Optionally and preferably, the method compares BNA pattern 20 to at least one baseline BNA pattern annotated as corresponding to a treated brain related disorder, and at least one baseline BNA pattern annotated as corresponding to an untreated brain related disorder.

The prognosis information can be transmitted to a computer-readable medium or a display device or a printing device, as desired.

The method ends at 17.

The BNA pattern comparison technique of the present embodiments can also be used for inducing improvement in brain function. In some embodiments of the present invention associated subject-specific BNA patterns are constructed for a subject during a higher-level cognitive test, generally in real time. The subject can be presented with the constructed BNA patterns or some representation thereof and use them as a feedback. For example, when, as a result of the cognitive action, the BNA pattern of the subject becomes more similar to a characteristic BNA pattern of a healthy group, presentation of such a result to the subject can be used by the subject as a positive feedback. Conversely, when, as a result of the cognitive action, the BNA pattern of the subject becomes more similar to a characteristic BNA pattern of a brain-disorder group, presentation of such a result to the subject can be used by the subject as a negative feedback. Real time analysis of BNA patterns in conjunction with neurofeedback can optionally and preferably be utilized to achieve improved cortical stimulation using external stimulating electrodes.

FIG. 5 is a flowchart diagram of another method suitable for estimating the likelihood of brain concussion from neurophysiological data, according to various exemplary embodiments of the present invention. The method begins at 10 and optionally and preferably continues to 11 at which the neurophysiological data are received, as further detailed hereinabove. The method continues to 12 at which relations between features of the data are determined so as to indentify activity-related features, and to 13 at which a subject-specific BNA pattern is constructed as further detailed hereinabove. In the present embodiment, the subject-specific BNA pattern is constructed using reference data which is group data or synthetic data. The constructed subject-specific BNA is associated with brain concussion.

The method proceeds to 51 at which the subject-specific BNA pattern (e.g., pattern 20) is compared to a group BNA pattern which is annotated as corresponding to brain concussion. The comparison can be performed as described above, so as to calculate a BNA pattern similarity. The method continues to 52 at which the similarity is compared with a recorded similarity describing comparison between a previously constructed subject-specific BNA pattern of the same subject and the same group BNA pattern. The method continues to 53 at which the likelihood of brain concussion is assessed responsively to a difference between the recorded similarity and the calculated similarity. Thus, the difference between method 50 and method 10 above is that in method 50 the assessment is based on observed changes in the calculated similarity and not necessarily on the change in the subject-specific BNA pattern. Another difference is the type of baseline BNA pattern which is employed. In method 10, the baseline BNA pattern is preferably subject-specific. In method 50, the baseline BNA pattern is a group BNA pattern.

From 52 the method can optionally and preferably loop back to 12 or 13 to construct another subject-specific BNA pattern. For example, the method can construct 13 a subject-specific BNA pattern which is associated with normal brain function and compare it 51 to a group BNA pattern which is annotated as corresponding to normal brain function to provide a second similarity level. The method can then compare 52 the second similarity with a respective second recorded similarity. In these embodiments the assessment is based also on the difference between the second recorded similarity and the second calculated similarity. For example, when the similarity that correspond to brain concussion is increased with time and the similarity that correspond to normal brain function is decreased with time, the method can assess that it is likely that the subject is suffering from concussion.

Method 50 optionally and preferably continues to 16 at which prognosis information is extracted responsively to the calculated similarities, as further detailed hereinabove.

The method ends at 57.

Methods 10 and 50 can also be combined. In these embodiments, the subject-specific is compared both to a subject-specific baseline and to a group annotated baseline. Each comparison provides further assessment regarding the likelihood of brain concussion. All the obtained assessments can be transmitted to a computer-readable medium or a display device or a printing device, as desired.

According to an aspect of some embodiments of the present invention there is provided a system for analyzing neurophysiological data. The system comprises a data processor, e.g., a dedicated circuitry or a general purpose computer, configured for receiving the neurophysiological data, and executing at least some of the operations described herein.

According to an aspect of some embodiments of the present invention there is provided a method of assessing a likelihood of attention deficit hyperactivity disorder (ADHD). The method comprises: identifying activity-related features in neurophysiological data acquired from the brain of a subject, constructing a BNA pattern, and calculating a BNA pattern similarity describing a comparison between the constructed BNA pattern and a baseline ADHD BNA pattern. The identification of the activity-related features and/or the construction of BNA pattern, can be done as described above with respect to the method for estimating the likelihood of brain concussion. Alternatively or additionally, the identification of the activity-related features and/or the construction of BNA pattern can be according to the teachings of PCT Application No. PCT/IL2011/000055, the contents of which are hereby incorporated by reference.

In various exemplary embodiments of the invention the baseline ADHD BNA pattern has nodes representing event related potentials, predominantly at one or more frequency bands selected from the group consisting of delta, theta and alpha frequency bands, at a plurality of frontocentral locations within a characteristic time window of from about 100 ms to about 200 ms. In some embodiments of the present invention the baseline ADHD BNA pattern has nodes representing event related potentials, predominantly at the delta frequency band at a plurality of occipital, parietal and frontocentral locations within a characteristic time window of from about 300 ms to about 600 ms.

Once the BNA similarity between the constructed BNA pattern and the baseline ADHD BNA pattern is calculated, it can be used for assessing the likelihood. For example, a BNA pattern similarity which is above a predetermined threshold can indicates a likelihood of the subject having ADHD.

The likelihood is optionally and preferably extracted by determining an ADHD index based, at least in part, on the similarity between the constructed BNA pattern and the baseline ADHD BNA pattern. The ADHD index can be the similarity itself or it can be calculated based on the similarity. In various exemplary embodiments of the invention the ADHD index is calculated based on the similarity between the constructed BNA pattern and a BNA pattern annotated as abnormal, as well as the similarity between the constructed BNA pattern and the baseline ADHD BNA pattern. For example, denoting the former similarity by $S_{normal}$ and the latter similarity by $S_{ADHD}$, where both $S_{normal}$ and $S_{ADHD}$ are between 0 and 1, the ADHD index $I_{ADHD}$ can be calculated as:

$$I_{ADHD} = (S_{ADHD} + (1 - S_{normal}))/2.$$

Variations of the above formula are not excluded from the scope of the present invention.

The brain-disorder index can be presented to the user graphically on a scale-bar.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

This example describes a model of a model for cognitive impairment brought upon by concussion. The model is based on administering scopolamine to healthy subjects.

Subjects were administered with Scopolamine 0.4 mg, and a placebo drug. Two group BNA patterns (one BNA pattern for the placebo group and one BNA pattern for the scopolamine group), and several subject-specific BNA patterns were constructed according to the teachings of the present embodiments.

Subjects performed several tasks, including the auditory oddball test, and the working memory test.

In the auditory oddball target detection test, the subjects were requested to respond to auditory target stimuli that occur infrequently and irregularly within a series of standard stimuli. The standard stimulus was in the form of a 1000 Hz tone, and the target stimulus was in the form of a 2000 Hz tone. The intervals between two successive stimuli (standard or target) were 1.5 seconds. Each subject was exposed to a series of stimuli, of which 80% were standard stimuli and 10% were target stimuli. The additional 10% were background sounds (referred to as "novel stimuli").

In the working memory test, each subject was requested to memorize an image of a human face (referred to as the "cue"). Two seconds later, the subject was again presented with an image of a human face (referred to as the "probe") and was asked to determine whether the probe matches the cue.

The tests and data acquisitions were performed in three time points (i) immediately following administration of placebo, (ii) one hour after administration of 0.4 mg of scopolamine, and (iii) two weeks afterwards, allowing complete washout of the drug. The BNA constructed from data acquired following administration of placebo was used as the baseline BNA. The effect of the drug is temporary, thus allowing the present inventors to simulate a concussion episode (when the pharmacokinectics of the drug are at peak level) and after recovery (when the drug has already washed out from the subject).

FIGS. 6A-C show results corresponding to three different subjects. Data were collected during the oddball test. Each of FIGS. 6A-C shows a group baseline BNA pattern annotated as normal, and two subject-specific BNA patterns acquired at time points (ii) and (iii). Also shown is the BNA pattern of the control group. The bar graph shows the similarity levels to the baseline. The normal range is indicated as a rectangle on the bar graph. More specifically, the rectangle denotes the minimal important difference (MID), which is calculated from the normal group data. Any change between two measures of a single subject, in this case the BNA score before and after the simulated concussion, that is outside the range of the MID, is considered a significant change. A change within the MID is considered non significant and can be viewed as noise of the system. A shown there is a clear significant change.

FIGS. 7A-C show results of experiments performed for the same three subjects. Data were collected during working memory test. Each of FIGS. 7A-C shows a group baseline BNA pattern annotated as normal, and two subject-specific BNA patterns acquired at time points (ii) and (iii). Also shown is the BNA pattern of the control group. The bar graph shows the similarity levels to the baseline. The normal range is indicated as a rectangle on the bar graph as described above with respect to FIGS. 6A-C.

As shown in FIGS. 6A-C and 7A-C, the similarity level to the normal baseline is reduced for the impaired condition, indicating that the likelihood of brain concussion is high. This example, demonstrates that ability of the present embodiments to assess the likelihood of brain concussion.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of estimating the likelihood of brain concussion from neurophysiological data acquired from the brain of the subject, comprising:
    by a set of electrodes placed on a scalp of a subject, acquiring the neurophysiological data from the brain of the subject; and
    using a data processor for:
    identifying activity-related features in said data wherein each feature is a vector of data characteristics;
    clustering said vectors to provide a plurality of clusters;
    calculating for at least one pair of clusters, at least one cluster property selected from the group consisting of (i) a number of vectors in a corresponding pair of clusters; (ii) a variability among numbers of vectors in said corresponding pair of clusters; (iii) a width of time windows associated with each cluster of said corresponding pair of clusters; (iv) a latency difference separating said corresponding pair of clusters;
    constructing a subject-specific brain network activity (BNA) pattern having a plurality of nodes, wherein each node represents a cluster of said plurality of clusters, and wherein each pair of nodes is assigned with a connectivity weight which comprises a weight index calculated based on said calculated properties;
    storing said constructed BNA pattern in a memory;
    retrieving said constructed BNA pattern and a baseline BNA pattern being specific to the subject from said memory;

calculating a BNA pattern similarity describing a comparison between said constructed BNA pattern and said baseline BNA pattern;

assessing the likelihood of brain concussion responsively to said BNA pattern similarity; and generating on a display an output indicative of said likelihood.

2. The method according to claim 1, wherein said baseline BNA pattern is based on a group BNA pattern characterizing a group of subjects identified as having normal brain function.

3. The method according to claim 1, wherein said baseline BNA pattern is based on a group BNA pattern characterizing a group of subjects identified as having a brain concussion.

4. The method according to claim 1, further comprising repeating said construction of subject-specific BNA and said calculation of BNA pattern similarity at least once.

5. The method according to claim 1, further comprising repeating said construction of subject-specific BNA and said calculation of BNA pattern similarity at least once, wherein each subject-specific BNA is constructed based on different reference data or model but using the same neurophysiological data of the subject, wherein each subject-specific BNA is compared to a baseline BNA pattern being associated with a different brain condition, and wherein said assessment is responsively to at least two BNA pattern similarities.

6. The method according to claim 5, wherein at least one baseline BNA pattern characterizes a group of subjects identified as having normal brain function, and at least one baseline BNA pattern characterizes a group of subjects identified as having a brain concussion.

7. The method according to claim 1, further comprising determining a concussion index based on at least said BNA pattern similarity.

8. The method according to claim 1, further comprising constructing several BNA patterns corresponding to different time intervals, and displaying said BNA patterns on a time axis.

9. The method according to claim 1, further comprising extracting prognostic information regarding a brain condition, responsively to at least said BNA pattern similarity.

10. The method according to claim 1, wherein said identifying said activity-related features comprises, identifying features and relations among features in the neurophysiological data of the subject, and comparing said features and said relations among features to features and relations among features of reference neurophysiological data.

11. The method according to claim 10, wherein said reference neurophysiological data corresponds to data acquired from a group or a sub-group of subjects.

12. The method according to claim 10, wherein said reference neurophysiological data corresponds to history data previously acquired from the same subject.

13. The method according to claim 10, wherein said reference neurophysiological data comprise data synthesized from a neurophysiological model.

14. The method according to claim 10, wherein said features and relations among features of said reference data are provided as at least one previously annotated BNA pattern.

15. The method according to claim 1, wherein said at least one cluster property is also selected from the group consisting of: (v) amplitude of a signal associated with said corresponding pair of clusters; (vi) frequency of a signal associated with said corresponding pair of clusters; and (vii) the width of a spatial window defining said clusters.

16. The method according to claim 1, wherein said neurophysiological data comprises data acquired before, during and/or after a treatment.

17. The method according to claim 16, further comprising assessing the effect of said treatment by comparing a BNA pattern similarity calculated using at least said baseline BNA pattern and a subject-specific BNA pattern constructed based on data acquired before a treatment, to a BNA pattern similarity calculated using at least said baseline BNA pattern and a subject-specific BNA pattern constructed based on data acquired after a treatment.

18. The method according to claim 16, further comprising assessing the effect of said treatment by comparing a BNA pattern corresponding to data acquired before a treatment to a BNA pattern corresponding to data acquired during and/or after a treatment.

19. The method according to claim 16, wherein said treatment comprises a pharmacological treatment employing an active agent.

20. The method according to claim 19, wherein said active agent is selected from the group consisting of scopolamine, ketamine, methylphenidate, donepezil, physostigmine, tacrine, fluoxetine, carbamazepine, amantadine, apomorphine, bromocriptine, levodopa, pergolide, ropinirole, selegiline, trihexyphenidyl, atropine, scopolamine, glycopyrrolate, baclofen, diazepam, tizanidine and dantrolene.

21. The method according to claim 16, wherein said treatment also comprises a placebo treatment employing a placebo agent, and wherein the method comprises assessing the effect of said pharmacological treatment by comparing a BNA pattern corresponding to data acquired during and/or after said a placebo treatment to a BNA pattern corresponding to data acquired during and/or after said pharmacological treatment.

22. The method according to claim 16, wherein said treatment comprises a surgical intervention.

23. The method according to claim 16, wherein said treatment comprises a rehabilitative treatment.

24. The method according to claim 16, wherein said treatment comprises phototherapy.

25. The method according to claim 16, wherein said treatment comprises hyperbaric therapy.

26. The method according to claim 16, wherein said treatment comprises at least one treatment selected from the group consisting of neural feedback, EMG biofeedback, EEG neurofeedback, transcranial magnetic stimulation (TMS) and direct electrode stimulation.

27. The method according to claim 1, further comprising acquiring said neurophysiological data from the brain of the subject, before, during and/or after the subject is performing or conceptualizing performing a task selected from the group consisting of a lower-level cognitive task and a higher-level cognitive task.

28. A computer software product, comprising a non-transitory computer-readable medium in which program instructions are stored, which instructions, when read by a data processor, cause the data processor to receive neurophysiological data and execute the method according to claim 1.

29. The method of claim 1, further comprising treating the subject for the brain concussion by at least one of: a surgical intervention, a rehabilitative treatment, phototherapy, hyperbaric therapy neural feedback, EMG biofeedback, EEG neurofeedback, transcranial magnetic stimulation, and direct electrode stimulation.

30. A method of estimating the likelihood of brain concussion from neurophysiological data acquired from the brain of the subject, comprising:
by a set of electrodes placed on a scalp of a subject, acquiring the neurophysiological data from the brain of the subject; and
using a data processor for:
identifying activity-related features in said data wherein each feature is a vector of data characteristics;
clustering said vectors to provide a plurality of clusters;
calculating for at least one pair of clusters, a plurality of cluster properties selected from the group consisting of (i) a number of vectors in a corresponding pair of clusters; (ii) a variability among numbers of vectors in said corresponding pair of clusters; (iii) a width of time windows associated with each cluster of said corresponding pair of clusters; (iv) a latency difference separating said corresponding pair of clusters;
constructing a first subject-specific brain network activity (BNA) pattern having a plurality of nodes, wherein each node represents cluster of said plurality of clusters, and wherein each pair of nodes is assigned with a connectivity weight which comprises a weight index calculated based on said calculated properties, said subject-specific BNA pattern being associated with brain concussion;
storing said constructed first BNA pattern in a memory;
retrieving said constructed BNA pattern and a first baseline BNA pattern annotated as corresponding to brain concussion;
calculating a first BNA pattern similarity describing a comparison between said first BNA pattern and said first baseline BNA pattern;
comparing said similarity with a first recorded similarity describing comparison between a previously constructed subject-specific BNA pattern of the subject and said first baseline BNA pattern;
assessing the likelihood of brain concussion responsively to a difference between said recorded similarity and said calculated similarity; and
generating on a display an output indicative of said likelihood.

31. The method according to claim 30, further comprising constructing a second subject-specific BNA pattern associated with normal brain function;
calculating a second BNA pattern similarity describing a comparison between said second BNA pattern and a second baseline BNA pattern annotated as corresponding to normal brain function; and
comparing said second similarity with a second recorded similarity describing comparison between a previously constructed subject-specific BNA pattern of the subject and said second baseline BNA pattern;
wherein said assessment is responsively also to a difference between said second recorded similarity and said second calculated similarity.

32. A system for estimating the likelihood of brain concussion, comprising,
a set of electrodes placeable on a scalp of a subject for acquiring neurophysiological data from the brain of the subject;
a data processor configured for:
receiving the neurophysiological data and identifying activity-related features in said data, each feature being a vector of data characteristics;
clustering said vectors to provide a plurality of clusters;
calculating for at least one pair of clusters, a plurality of cluster properties selected from the group consisting of (i) a number of vectors in a corresponding pair of clusters; (ii) a variability among numbers of vectors in said corresponding pair of clusters; (iii) a width of time windows associated with each cluster of said corresponding pair of clusters; (iv) a latency difference separating said corresponding pair of clusters;
constructing a subject-specific brain network activity (BNA) pattern having a plurality of nodes, wherein each node represents cluster of said plurality of clusters, and wherein each pair of nodes is assigned with a connectivity weight which comprises a weight index calculated based on said calculated properties;
storing said constructed BNA pattern in a memory;
retrieving said constructed BNA pattern and a baseline BNA pattern being specific to the subject from said memory;
calculating a BNA pattern similarity describing a comparison between said constructed BNA pattern and said baseline BNA pattern;
assessing the likelihood of brain concussion responsively to said BNA pattern similarity and
generating on a display an output indicative of said likelihood.

* * * * *